United States Patent [19]

Surgant, Sr. et al.

[11] Patent Number: 4,936,901

[45] Date of Patent: Jun. 26, 1990

[54] FORMULATIONS OF WATER-DISPERSIBLE GRANULES AND PROCESS FOR PREPARATION THEREOF

[75] Inventors: John M. Surgant, Sr., Ladue; John M. Deming, Hazelwood, both of Mo.

[73] Assignee: Monsanto Company, St. Louis, Mo.

[21] Appl. No.: 58,071

[22] Filed: Jun. 16, 1987

Related U.S. Application Data

[63] Continuation-in-part of Ser. No. 883,801, Jul. 9, 1986, abandoned.

[51] Int. Cl.$^5$ .............................................. A01N 43/58
[52] U.S. Cl. ............................................ 71/92; 71/86; 71/87; 71/88; 71/93; 71/94; 71/90; 71/100; 71/105; 71/107; 71/108; 71/110; 71/116; 71/117; 71/118; 71/120; 71/121; 71/125; 71/126
[58] Field of Search .............................. 71/93, 118, 92

[56] References Cited

U.S. PATENT DOCUMENTS

| | | | |
|---|---|---|---|
| 3,920,442 | 11/1975 | Albert et al. | 71/93 |
| 4,150,968 | 4/1979 | Young et al. | 71/93 |
| 4,280,833 | 7/1981 | Besstman et al. | 71/118 |
| 4,334,910 | 6/1982 | Lorincz et al. | 71/65 |
| 4,647,301 | 3/1987 | Los | 71/92 |

*Primary Examiner*—Richard L. Raymond
*Assistant Examiner*—Amelia A. Owens
*Attorney, Agent, or Firm*—William I. Andress; Gordon F. Sieckmann

[57] ABSTRACT

The invention herein relates to dry flowable water-dispersible granular formulations and to a process for the preparation thereof.

In particular, the water-dispersible granular formulations of this invention comprise a mixture of aggregates of microcapsules of water-insoluble pesticide, e.g., alachlor, or a plant growth regulant encapsulated within a polymeric shell wall and at least one other pesticide, e.g., atrazine or a salt of glyphosate, which is non-encapsulated.

The water-dispersible granular formulations of the invention are prepared by mixing appropriate quantities of an aqueous dispersion of the encapsulated component, the non-encapsulated component and formulation adjuvants to form a slurry of the desired viscosity which can be directly extruded than dried or the slurry in more dilute, less viscous form may be spray dried, or agglomerated in fluid beds or rotating disc agglomerators.

22 Claims, No Drawings

FORMULATIONS OF WATER-DISPERSIBLE GRANULES AND PROCESS FOR PREPARATION THEREOF

This is a continuation-in-part application of co-pending U.S. Ser. No. 883,801, filed July 9, 1986, now abandoned.

BACKGROUND OF THE INVENTION

The invention herein relates to formulations of dry flowable, water-dispersible granules of mixtures of pesticides or plant growth regulators (or regulants) and to a process for the preparation thereof.

In particular, the water-dispersible granular formulations of this invention comprise a mixture of aggregates of microcapsules of a water-insoluble pesticide, e.g., alachlor, or plant growth regulator, e.g., EPTC, encapsulated within a polymeric shell wall and particles of another pesticide, e.g., atrazine, which are non-encapsulated.

The water-dispersible granular formulations of the invention are prepared by mixing appropriate quantities of an aqueous dispersion of the encapsulated herbicide or plant growth regulator, the non-encapsulated herbicide or plant growth regulant and formulation adjuvants to form a paste of the desired viscosity which can be directly extruded then dried and agglomerated or the paste in more dilute, less viscous or slurry form may be spray dried, or agglomerated in fluid beds or rotating disc agglomerators.

For some low melting solids/liquids, microencapsulation offers the only means of maintaining stable sprayable suspensions of that chemical in water. Having accomplished a stable suspension, microencapsulated pesticide or plant growth regulator formulations which are aqueous suspensions of microcapsules offer many desirable features. In some cases, reduced toxicity and extended activity of the encapsulated pesticide have been noted. Many pesticides decompose or volatilize quickly, thus reducing the effectiveness of the material; microencapsulation of such materials can postpone the decomposition of the pesticide. Microencapsulation of pesticidal materials can also enhance the safety of the pesticide for the applicator. Since the pesticide is enclosed in a polymeric shell wall the applicator is not directly exposed to the chemical. Another advantage of encapsulation of an active pesticidal agent lies in the possibility of a combination of substances that cannot be blended or are incompatible with one another, e.g., water-insoluble pesticides with water-soluble pesticides or water-soluble fertilizers.

For liquid products, microencapsulation can eliminate the cost, availability, flammability, toxicology disadvantages of solvents by permitting water to be used as the suspending medium. For solid formulations derived from solutions or suspensions, those advantages pertain to the process as well as to the end use of the product.

Various methods are known in the art for microencapsulation of water-insoluble pesticides via interfacial polymerization reaction. U.S. Pat. Nos. 4,360,376, 3,429,827, 3,577,515 and 4,280,833 provide a good summary of the methods which are available. U.S. Pat. No. 4,280,833 describes the microencapsulation of concentrated amounts of water-insoluble pesticide materials on the order of 480–700 grams per liter, this previously unattainable high concentration offers a distinct energy saving advantage when water driveoff is required to convert the liquid to a solid.

While it can be advantageous to encapsulate pesticidal materials, it is also advantageous to have the pesticidal material in dry form. Dry pesticide formulations can be stored for long periods of time, over wide extremes of temperature, without destroying the stability of the formulation. It is easier and less expensive to dispose of containers in which dry pesticidal materials are stored since these are most often made of paper, which can be safely burned if the solid empties completely from the bag leaving no residue. Still more preferable is the use of water-soluble plastic bags in which to store, ship and add to water the water-dispersible granules or other dry-form pesticides. Shipping costs can be reduced since the solvent or water carrier of emulsifiable concentrates and water-based flowable pesticide formulations is eliminated. The most common types of dry pesticide formulations are wettable powder and granule formulations. The preparation of each type of formulation is known.

Various methods are described in the technical and patent literature for producing various forms of encapsulated products for pesticidal materials. Typically, the encapsulated product may be in the form of microcapsules of encapsulated material suspended in a carrier (continuous) medium or in the form of dried microcapsules, powders, granulates, microgranulates or water-dispersible granules. Examples of the foregoing products may be found in British Patent No. 2,042,892 and in the following U.S. Pat. Nos.: 3,429,827, 4,244,836, 4,309,213, 3,737,337, 4,157,983, 4,235,872, and 3,577,515.

Other forms of water-dispersible, granular, non-encapsulated products are described in U.S. Pat. Nos. 3,657,446, 3,639,617, 3,954,439, 2,870,059, 3,920,442, 4,511,395, 4,134,725, 4,183,740 and 3,854,981, in German Patent No. DT-1,642,122 and in So. African Patent Application No. 692053. The products produced in the above exemplified patents may be dried typically in an air flow, by evaporation, by spray drying, etc.

Yet another common form of pesticidal product mentioned above is the wettable powder, as exemplified in British Patent No. 2,037,585 and U.S. Pat. Nos. 3,791,811 and 3,731,551.

The most common wettable powder pesticide formulation is one in which fine particles of a high melting solid, crystaline pesticide are combined with a finely divided solid carrier, e.g., silicates or alumino silicates comprising single lattice or double lattice clays. The surface active agents allow the concentrate to be diluted in water to field strength to form stable, sprayable suspensions. Most high melting solid pesticides can be processed as a wettable powder; in the 60–90% concentration range; the main requirement being that they exhibit appropriate chemical compatibility with the finely divided, solid carrier. In order for low melting actives to be formulated as wettable powders they must first be absorbed into highly porous media such as diatomaeous earth, pearlite or manufactured silicas to a degree that the mixture exhibits the properties of a solid. This dilution essentially reduces wettable powder concentrations of liquids to less than 60%, with 40–50% a more common range. Further, low melting actives which undergo a phase change at ambient storage temperatures (e.g., $-10°$ to $+50°$ C.) usually present such a caking problem from crystal formation and growth that the use of an absorbing agent is futile and cake-free solid formulations having concentrations of >20% are impossible to attain. Alachlor and trillate are excellent examples of such chemicals.

The primary disadvantage of wettable powder pesticide formulations is that they tend to be dusty, posing health problems to the applicator if the pesticide material is irritating or toxic and handling problems during the preparation of the material. Further, wettable powders tend to have low bulk density and, thus, do not wet up rapidly when added to water. Inability to wet up can result in excessive mixing times and/or the formation of "lumps" of wettable powder in the water. These lumps are difficult to disperse in the water making it difficult to get even distribution of the pesticide throughout the water and, thus, even application of the pesticide when applied. In extreme cases, lumping can result in clogging of sprayer nozzles.

A granular pesticide formulation is one which usually involves impregnation of molten pesticidal agent into the pores of a preformed granule, but may involve agglomeration of high melting solids with powdered inerts such as clay. For impregnation, the active ingredient must be a liquid at a temperature below about 120° C. or be compatible with a liquid carrier which can take solubilized or suspended active ingredients into the pores of the granule during a liquid-solid blending operation. Common granule carriers are clays, attapulgite, bentonite, sepiolite and the like.

Granular pesticides comprising high-melting solids may also be formed by extrusion, agglomeration or core coating.

A disadvantage of some conventional granule pesticide formulations is that the total amount of active pesticide carried on the granule is limited by carrier, equipment metering and efficacy considerations to 5–25% loadings. These low loadings contribute to the expense of the granules. This, and the added expense of separate granular application equipment, are economic limitations on granule use. Caking can be a problem if the active pesticidal agent readily migrates to the surface of the granule making it "sticky". Finally, since many granules are irregularly shaped, some dusting occurs as the granules wear against each other in the package during storage and handling.

Although, as indicated above, water-dispersible granules are generally known and have been commercially available for sometime now, the present invention affords an economical means of making water-dispersible granules from chemicals and combinations thereof having a wide range of melting points, including low melters. The process according to this invention permits the formation of granules having a particularly advantageous structure and physical properties and formulation compatible with that process.

As will be described in more detail herein, the water-dispersible granule components of the invention are, therefore, a combination of an aggregate of small polymeric microcapsules containing the water-insoluble pesticide or plant growth regulator and a non-encapsulated pesticide or plant growth regulant. The geometry and composition of the water-dispersible granules of the invention permit them to be free flowing and relatively dust-free. Since one of the active pesticidal agents is encapsulated, and the other pesticide(s) is of microcapsule dimension, although non-encapsulated, the water-dispersible granules of the invention pose very little hazard to the user when handled.

Another advantage of microencapsulated water-dispersible granules is the ability to produce a product package containing a plurality of pesticides wherein antagonistic action between the pesticides is reduced or eliminated by means of the capsule shell.

The water-dispersible granules of the invention have bulk densities sufficiently high to readily wet-up when added to the water in a farmer's spray tank thus eliminating the wetting or lumping problem of wettable powders.

The water-dispersible granules of the invention immediately reconstitute when added to water; by that it is meant that the large aggregates dissociate or break apart into the tiny, individual microcapsules which disperse to their original pre-agglomerated form throughout the water. Since the pesticide is encapsulated, one can get a high degree of loading of the active, on the order of 65–90% active pesticidal agent for water-dispersible granule as contrasted to the maximum 50% loading attainable with commercially available granules. Further, one is able to add the encapsulated pesticide to aqueous solutions, e.g., liquid fertilizer solutions which might ordinarily be antagonistic to the unencapsulated pesticide.

SUMMARY OF THE INVENTION

The present invention relates to a pesticidal or plant growth regulant composition comprising water-dispersible granules and formulations thereof. As a collective mass, the granules of the invention are free-flowing, relatively dust free, non-caking and disperse immediately in aqueous media.

The water-dispersible granules of the invention comprise a mixture of an aggregation of individual essentially spherical microcapsules of one or more water-insoluble pesticides or plant growth regulants encapsulated within a polymeric shell wall and particles of at least one non-encapsulated pesticide or plant growth regulant. Upon contact with an aqueous medium, the granules of said aggregation of encapsulated pesticides and nonencapsulated pesticides or plant growth regulants disintegrate to release the individual microcapsules of encapsulated material which, together with said non-encapsulated material disperse uniformly throughout said aqueous medium.

In alternative embodiments of the invention, the non-encapsulated component can be either a water-soluble or water-insoluble pesticide or plant growth regulant; so, too, other additaments, e.g., herbicide safeners (antidotes) or formulation adjuvants, can be included with the pesticide or plant growth regulant.

Further modifications of the invention contemplate that a given component, e.g., a water-insoluble pesticide or plant growth regulant normally useful as the encapsulated component, may be used as the non-encapsulated component and some other water-insoluble component, e.g., an insecticide or other pesticide, used as the encapsulated component.

The optimum particle size distribution of the water-dispersible granules should be such that from about 90–95% of the granules have diameters within the range of about 180–420 microns, although larger particle-size granules, up to about 850 microns will function satisfactorily; however, these larger particles reconstitute more slowly. Aggregates less than about 150 microns will tend to result in wind drift, dry flowability and wetting problems. Typical particle size distribution for the granules herein is as follows:

60–75% will pass through 40 mesh and be retained on 60 mesh screen (U.S. Standard Sieve Series), i.e., 40/60 sieve screens; 420–250 microns;
30–15% on 60/80 sieves; 250–180 microns;
8–9% on 80/100 sieves; 180–150 microns;
2–1% less than 150 microns.

The moisture content of the water-dispersible granules herein should be within the range of about 0.1–8 percent maximum and, preferably, no more than 4% moisture and still more preferably, within the range of 1–2 weight percent.

The water-dispersible granules of this invention should have a suitable bulk density within the range of about 23–96 kg/m$^3$ preferably about 48–96 kg/m$^3$, with about 56–72 kg/m$^3$ being an optimum bulk density.

A further embodiment of the invention relates to formulations of the above-described aggregates of water-dispersible granules together with necessary formulation adjuvants or surfactants, including emulsifier, binders, dispersants, separators, detackifiers, etc., which create a separating and bridging connection between the microcapsules within said granules and between the aggregated granules themselves to aid in preventing fusion, caking and attrition therebetween and caking of the dry aggregate mass during storage. Of the various formulation adjuvants, some of the more effective ones are inorganic salts, e.g., a chloride, nitrate or sulfate of ammonium or of an alkali metal or alkaline earth metal, such as sodium, potassium or calcium, zinc, copper, manganese or magnesium be present as a binder/dispersant to aid in reconstitution of the aggregates when mixed with water.

In some embodiments, it is unnecessary to add a separate formulation adjuvant. For example, in water-dispersible granules containing salts of glyphosate, those salts themselves serve to function as a binder/separator. However, for greater biological efficacy an additional surfactant or binder/separator is preferably added to the water-dispersible granule.

The adjuvants or surfactants may be used in different ratios relative to each other. For example, a preferred binder/separator combination includes ammonium sulfate and a Witconate salt or other surfactant in ratios within the range of about 1:1 to 24:0:1.0.

Rapid removal of water in the spray-drying process minimizes component migration and, therefore, maintains the homogeneous distribution of separating aids between the microparticles.

The formulations of this invention comprise a mixture of one or more water-insoluble pesticides, e.g., herbicides, insecticides, fungicides, nematocides, miticides, etc., or plant growth regulants, encapsulated within the microcapsules and at least one other water soluble or water-insoluble non-encapsulated pesticide or plant growth regulant forming the water-dispersible granules. Variations of combination of herbicides include those wherein but one of them is encapsulated, while one or more other herbicides remain unencapsulated. The concentration of the pesticide should be, minimally, sufficient to be pesticidally effective and can range upwardly to 90% by weight. Suitable concentration ranges are from about 0.1% to 90% and, typically, from about 5 to 85% by weight.

The weight ratio of the encapsulated component to the non-encapsulated suitably is within the range of about 50:1 to 1:50, preferably 20:1 to 1:1 and more preferably 16:1 to 1:1. In some combinations, e.g., where the encapsulated herbicide is alachlor and the non-encapsulated herbicide is atrazine, the ratio of the encapsulated to non-encapsulated herbicide is preferably about 1.0:1.0 to 3.0:1.0. When acetochlor is substituted for alachlor, the preferred acetochlor:atrazine ratio would be 1.0:2.0 to 2.0:1.0. In the combination of alachlor:imazaquin the ratio would be about 12:1 to 20:1 and for acetochlor:imazaquin, about 8.0:1 to 16:1.0. In combinations of an acetanilide, e.g., alachlor, with a salt of glyphosate, e.g., the mono-sodium or mono-potassium or mono-ammonium salt of glyphosate, the acetanilide:glyphosate ratio suitably would range from about 1.0:1.0 to about 4.0:1.0.

Additional embodiments include the encapsulation of safeners or antidotes for herbicides together with the herbicides within the same shell wall or the safener may be situated in the interstices between or on the surface of the microcapsules.

A further embodiment of the invention relates to a process for preparing the above-described water-dispersible granules which comprises:
(a) forming a paste or slurry of an admixture comprising:
(i) an aqueous suspension comprising microcapsules containing at least one water-insoluble pesticide or plant growth regulant encapsulated within a solid polymeric shell wall,
(ii) one or more additional water-soluble or water-insoluble pesticides or plant growth regulants which are non-encapsulated, and, optionally,
(iii) formulation additives, and
(b) fluidizing said paste or slurry in a form suitable for direct agglomeration or extrusion followed by agglomeration, and
(c) agglomerating said granular formulations as an admixture comprising at least one encapsulated pesticide and at least one non-encapsulated pesticide by drying.

DETAILED DESCRIPTION OF THE INVENTION

In a primary aspect, the invention is directed to a pesticide or plant growth regulant product comprising free flowing, essentially-spherical water-dispersible granules wherein said water-dispersible granules comprise an admixture of at least one water-insoluble pesticide or plant growth regulant encapsulated in a polymeric shell wall and at least one non-encapsulated component, e.g., a pesticide and/or a plant growth regulant or safener, together with formulation adjuvants. Said granules are, optimally, from about 180 to about 420 microns in diameter and may contain up to 8% preferably no more than about 6% and, optimally, about 1.0 to about 2.0% by weight moisture. The individual water-dispersible granules are an admixture of (1) an aggregation of individual spherical microcapsules which contain at least one water-insoluble pesticide or plant growth regulant within a polymeric shell wall and (2) at least one non-encapsulated component, e.g., a pesticide, and readily disintegrate upon contact with water to release said individual particles.

As noted above, another aspect of the invention relates to formulations of said granules and formulation adjuvants.

The invention is further directed to a process for preparing water-dispersible granules and formulations as described above.

As used herein, the term "pesticide(s)" refers to active compounds which serve primarily to kill or destroy plant or animal life. The term "herbicides" is used to signify compounds which primarily are used to kill plant life and the term "biocide(s)" will refer broadly to compounds which are intended to kill various forms of animal life. Exemplary biocides include insecticides, fungicides, nematicides, miticides, etc., which are designed primarily to kill, respectively, insects, fungi, nematodes, mites, etc.

The term(s) "plant growth regulator(s)" or "plant growth regulant(s)" as used herein connotes a product which serves to modify the normal sequential development of a treated plant to agricultural maturity without killing the plant. Such modification may result from the effect of the material on the physiological processes of the plant or from the effect of said material on the morphology of the plant. Those modifications may also result from any combination or sequence of physiological or morphological factors. It, is well known that some compounds can function as a herbicide when applied to the plant at moderate or high application rates, yet also function as a plant growth regulant when applied at low to minute application rates. Examples of such compounds include glyphosate, CDAA, amidochlor, EPTC, etc.

The term "aggregate", or grammatical variations thereof, as used herein refers to the collection, agglomeration or aggregation of individual, small spherical microcapsules of the encapsulated component of the mixed pesticide or plant growth regulant into a larger, generally spherical particle which together with the non-encapsulated component, e.g., a pesticide, is referred to herein as water-dispersible granule. When the dry, free-flowing water-dispersible granules of the invention are added to water for application to the soil or plants, they disassociate into small, spherical microcapsules of the encapsulated water-insoluble component(s) and the non-encapsulated component(s). These encapsulated and non-encapsulated components disperse throughout the water forming an aqueous suspension; i.e., solids dispersed throughout an aqueous liquid.

As used herein the term "dry" or "dry-flowable" refers water-dispersible granules having a moisture content of no greater than 8% by weight.

By "free-flowing" is meant that the water-dispersible granules are essentially free of caking or fusing of the granules and are freely pourable, as from one container to another.

The dry, free-flowing water-dispersible granules of the invention are prepared by drying, preferably spray drying, a slurry comprising an aqueous suspension comprising microcapsules containing one or more water-insoluble pesticide or plant growth regulant within a polymeric shell wall together with at least one non-encapsulated pesticide or plant growth regulant and formulation adjuvants. In formulations of herbicidal water-dispersible granules, a safener may be incorporated either within or externally of the encapsulant shell wall. Said slurry is fluidized in a form suitable for direct agglomeration (i.e., formation, aggregation and collection of said water-dispersible granules) or extrusion followed by agglomeration, by drying, preferably by spray drying, but alternatively, by means of fluid beds or by rotating disc agglomerators. As the water is removed from the fluidized slurry, aggregates or agglomerates of essentially spherical microgranules, referred to herein as a water-dispersible granules, are formed and collected.

As used herein, the term "aqueous suspension" refers to a two-phase system in which solid particles; i.e., small, spherical microcapsules containing a water-insoluble pesticide(s) or plant growth regulant(s) or other additaments, interspersed with a high-melting water-insoluble pesticide(s) plant growth regulant or other additaments are suspended in an aqueous (continuous) phase liquid. The aqueous suspension may contain, in addition to the microcapsules and the emulsifier which was used in the process of microencapsulation, small amounts of other water-soluble materials, e.g., safeners, salts, emulsifiers, dispersants, lower alkylene glycol, etc. and finely divided solids, e.g., clays and silicas. In an alternative embodiment the aqueous suspension may comprise the encapsulated component as the suspended solid component in an aqueous phase which contains a water-soluble component(s), e.g., a water-soluble herbicide such as mono-salt of glyphosate. Such materials are described in greater detail hereinafter.

The small, individual microcapsules of the encapsulated component and particles of non-encapsulated component do not fuse or become integrally attached to each other during the spray drying operation. They remain discrete, individual, particles which are separated from and bridged to each other by a thin layer of salts and emulsifier which is left behind when water is rapidly removed from the aqueous suspension.

It is, thus, an advantage of the preferred spray drying process used to make the agglomerated microcapsules herein that the formulation aids are kept from migrating from their desired locations between the granules. The more important separation aids appear to be inorganic salts such as the alkali metal and alkaline earth metal halides, e.g., NaCl, KCl, CaCl$_2$ and (NH$_4$)$_2$SO$_4$, and the Witconate salts, e.g., Witconate 90, Witconate AOS, ($\alpha$-olefin sulfonate) etc. and a minimum amount of water of hydration. Other separation means include surfactants, water-soluble polymers, higher alcohols and other water-soluble or dispersed components. Still other means to maintain good separation include maintenance of spray-drying temperatures below the fusion temperature of the granule shell. This may be done by a combination of the temperature and product moisture content at the spray tower exit and product feed mode. For example, using the counter-current feed mode, at a moisture content of 1-3 weight %, the exit temperature should be within the range of about 122°-149° C. or at 8-10% moisture, the temperature can be within the range of about 93°-121° C.

There are several techniques known for micro-encapsulating pesticide materials; see for example MICROENCAPSULATION PROCESSES AND APPLICATIONS edited by Jan E. Vandegaer, 1974 Plenum Press, New York and London. Such processes include coacervation encapsulation, interfacial condensation polymerization, and fluid bed coating. The preferred method for use herein is interfacial polycondensation microencapsulation and especially the process described by U.S. Pat. No. 4,280,833 as well as Ser. No. 619,752 filed June 12, 1984, Ser. No. 655,827 filed Oct. 1, 1984, and Ser. No. 566,108 filed Dec. 27, 1983, all of which describe encapsulation of concentrated amounts of water-insoluble pesticides, i.e., greater than 480 grams of water-insoluble material per liter of total composition. High concentration microencapsulation is achieved by use of specific emulsifiers and these higher starting concentrations are of both energy and process benefit in accomplishing a dry product.

Briefly, microencapsulation via interfacial condensation polymerization reaction involves encapsulating a water-immiscible material within a shell wall of polycondensate, e.g., polyurea, polyamide, polysulfonamide, polyester, polycarbonate, or polyurethane by (1) providing an aqueous solution containing an emulsifier capable of forming a stable oil-in-water emulsion when concentrated amounts of discontinuous phase liquid are present vis-a-vis the continuous or aqueous phase liquid; (2) forming an organic or discontinuous phase liquid which consists essentially of the water-insoluble pesticide or plant growth regulant (the material to be encapsulated) with a first shell wall monomer dissolved therein; (3) addition of the discontinuous liquid to the aqueous phase, with agitation, to form a dispersion of small droplets discontinuous phase liquid throughout the aqueous phase i.e., an oil-in-water emulsion is formed); (4) addition of a second water-miscible shell wall monomer, with continued agitation, to the oil-in-water emulsion; and (5) reaction of the second shell wall monomer with the first shell wall monomer to form a polymeric shell wall about the water-insoluble pesticide.

At the completion of the encapsulation reaction there is an aqueous suspension which is a two-phase system wherein solid particles (microcapsules) are suspended in an aqueous (continuous) phase liquid. In addition to the solid particles, the aqueous liquid contains the emulsifier which was used in the encapsulation process. Additionally, various other materials may be added to the aqueous suspension which aid in spray drying or which aid in the disassociation of the water-dispersible granule when it is added to water, or, improves the non-caking, non-dusting, strength or flow characteristics of the granule in its spray-dried form. Such materials are hereinafter referred to as "suspension adjuvants", or when applied to the spray-dried granule as "agglomeration adjuvants".

As used herein the term "suspension adjuvant" refers to any material which is added to the aqueous suspension and which subsequently facilitates drying of the droplet of aqueous suspension during the spray dry process or which facilitates the disassociation of the water-dispersible granule when it is added to water or improves the dry strength and other characteristics of the granule. The suspension and agglomeration adjuvants useful herein are water-soluble salts, e.g., (NH$_4$)$_2$SO$_4$, NaCl, CaCl$_2$, water-soluble emulsifiers, or polymers e.g., polyvinyl pyrrolidone (PVP), polyvinyl alcohol (PVA) electrolytes, natural gums, or other additives, such as water-soluble alkylene glycols, finely divided solid particles, e.g., clays and silicas.

The water-insoluble pesticide(s) which is the active agent of the water-dispersible granule of the invention and which is encapsulated is suitably any liquid, oil, meltable solid, solvent-soluble, or copesticide-soluble active ingredient, into which the first shell wall monomer can be dissolved and which is non-reactive thereto. Such water-immiscible pesticides include as representative herbicides, e.g., α-chloro-2',6'-diethyl-N-methoxymethyl acetanilide (commonly known as alachlor), N-butoxymethyl-α-chloro-2',6'-diethylacetanilide (commonly known as butachlor), 2'-methyl-6'-ethyl-N-(1-methoxy-prop-2-yl)-2-chloroacetanilide (commonly known as metolachlor), 2'-t-butyl-2-chloro-N-methoxymethyl-6'-methylacetanilide, α-chloro-N-(2-methoxy-6-methylphenyl)-N-(1-methylethoxymethyl)-acetamide, α-chloro-N-(ethoxy-methyl)-N-[2-methyl-6-(trifluoro-methyl)phenyl]-acetamide, α-chloro-N-methyl-N-[2-methyl-6-(3-methylbutoxy) phenyl] acetamide, α-chloro-N-methyl-N-(2-methyl-6-propoxyphenyl)acetamide, N-(2-butoxy-6-methylphenyl)-α-chloro-N-methyl acetamide, N-(2,6-dimethylphenyl)-N-(1-pyrazolylmethyl)chloroacetanilide (common name "metazochlor"), N,N-diallyl-2-chloroacetamide (common name "allidochlor"), isobutyl ester of (2,4-dichlorophenoxy)acetic acid, 2-chloro-N-(ethoxymethyl)-6'-ethyl-o-acetotoluidide (commonly known as acetochlor), 1-(1-cyclohexen-1-yl)-3-(2-fluorophenyl)-1-methyl urea, S-2,3,3-trichloroallyldiisopropyl thiocarbamate (commonly known as "triallate"), S-2,3-dichloroallyldiisopropylthiocarbamate (commonly known as "diallate"), α,α,α-trifluoro-2, 6-dinitro-N,N-dipropyl-p-toluidine (commonly known as "trifluralin"), 2-(2-chlorophenyl)methyl-4,4-dimethyl-3-isoxazolidinone; 3,5-pyridinedicarbothioc acid, 2-(difluoromethyl)-4-(2-methylpropyl)-6-(trifluoromethyl)-, S,S-dimethylester; 3-pyridinecarboxylic acid, 2-(difluoromethyl)-5-(4,5-dihydro-2-thiazolyl)-4-(2-methylpropyl)-6-(trifluoromethyl)-, methyl ester; 3-pyridinecarboxylic acid, 2-(difluoromethyl)-4-(2-methylpropyl)-5-(1H-pyrazol-1-ylcarbonyl)-6-trifluoromethyl)-, methyl ester; 5-methyl-4-methoxycarbonyl-3-(3'-methoxycarbonylphenoxy)-pyrazole and 5-methyl-4-methoxycarbonyl-3-(3'-methoxyphenoxy) pyrazole.

Preferred among the acetamide/acetanilide class of herbicides are alachlor, butachlor, acetochlor, metolachlor, metazochlor, α-chloro-N-(ethoxymethyl)-N-[2-methyl-6-(trifluoromethyl)-phenyl]acetamide and α-chloro-N-(2-methoxy-6-methylphenyl)-N-(1-methylethoxymethyl)acetamide.

Preferred pyrazole and pyridine derivatives are those named above and in the relevant patents and patent applications identified hereinbelow.

A wide variety of pesticides, especially herbicides, or plant growth regulants can be used as the non-encapsulated component of the compositions of this invention. Such herbicides and plant growth regulants are from various classes of compounds including various water-soluble and water-insoluble derivatives of ureas, triazines, carbamates and the thio-, dithio- and thiol-variations thereof, acetamides, acetanilides, diphenyl and dinitrophenyl ethers, imidazolidines, N-phosphonomethylglycine (common name "glyphosate"), pyrazoles, pyridines, etc. Of particular interest and preference as the non-encapsulated herbicidal or plant growth regulator component of the water-dispersible granules of this invention are the water-soluble salts of N-phosphonomethyl glycine (common name "glyphosate"), particularly (for herbicides) the mono-alkali metal or ammonium salts, and the water-insoluble compounds 2-chloro-4-ethylamino-6-isopropylamine-1,3,5-triazine (common name "atrazine") and 2-[4,5-dihydro-4-methyl-4-(1-methylethyl)-5-oxo-1H-imidazol-2-yl]-3-quinoline carboxylic acid (common name "imazaquin").

Other suitable herbicides useful as the non-encapsulated component of the water-dispersible granules of this invention include, by common name, the following compounds (the chemistry of each of which is readily found in standard handbooks, e.g., Pesticide Manual of the British Crop Protection Council, Fifth Edition, January, 1977, edited by H. Martin et al):

| | | |
|---|---|---|
| Ametryne | Dalapon | Methabenzthiazuron |
| Aminotriazole | Desmedipham | Methazole |
| Ammonium Sulphamate | 2,4-D | Metoxuron |
| Barban | Desmetryne | Metribuzin |
| Bentazone | Dicamba | Monolinuron |
| Benzthiazuron | Dichlorbenil | Monuron |
| Bifenox | Dichlorprop | Naptalam |
| Bromacil | Dinitramine | Neburon |
| Bromofenoxim | Dinoterb | Paraquat |
| Bromophos-Ethyl | Diquat | Picloram |
| Bromoxynil | Diuron | Propanil |
| Bromoxynil Octanoate | DSMA | Propachlor |
| Brompyrazone | Fenoprop | Propazine |
| Chloramben | Fenuron | Pyrazon |
| Chloroxuron | Flometuron | Siduron |
| Chlorthal-Dimethyl | Isoproturon | Simazine |
| Chlorthiamid | Linuron | Simetryne |
| Chlortoluron | Maleic Hydrazide | 2,4,5-T |
| Cyanazine | MCPA | MCPB |
| Cycluron | Metamitron | |

It is one aspect of this invention that certain of the above-mentioned water-insoluble herbicides used as the non-encapsulated component may be used in alternative embodiments as the encapsulated component of the water-dispersible granules and vice-versa.

Certain high-melting herbicides, e.g., N-(3,4-dichlorophenyl)-N'-methoxy-N'-methyl-urea (commonly known as "linuron") 4-amino-6-tert-butyl-3-(methylthio-as-triazine-5-(4H)one (common name "metribuzin") when used as the encapsulated component, cannot be encapsulated directly, but must be solubilized by the water-insoluble co-pesticide(s) and the mixture then encapsulated.

Representative insecticidal pesticides which are non-encapsulated but may be included together with the encapsulated water-insoluble herbicide include, e.g., the following compounds (by common name): abamectin, aldecarb, acephate, aldrin, aminocarb, azinphos, bendiocarb, carbaryl, chlormephos, DDT, dicofol, difluben- zuron, endothion, fenofos, fenvalerate, heptachlor, methiocarb, methomyl, methyl-and ethyl-parathion, permethrin, pyrethrin, terbufos, etc.

Representative fungicidal pesticides which are non-encapsulated but may be included with the above encapsulated herbicides and/or insecticides include the following (by common name); anilazine, benodanil, benomyl, butacarb, captafol, captan, carboxin, chloranil, chlorbromuron, chloroneb, chlorthalnil, chlorquinox, dazomet, dichlofluanid, diclone, dichloraphen, dichloran, dithianon, dodine, ferbam, folpet, mancozeb, maneb, thiabendazole, thiram, zineb, ziram, etc. Other fungicides which are low-melting may be included together with low-melting insecticides and herbicides or plant growth regulants as the microencapsulated component of the water-dispersible granule. Examples of such fungicides are dinocat, edifenphos, Terrizole, Dowside-A, and pyrazophos.

Representative nematicides which may serve as the encapsulated component herein include, e.g., terbufos, fensulfothion, carbofuran, ethoprop, fenamiphos, dichloropropene, aldecarb and oxamyl.

Representative miticides which may be used in the encapsulated component of the present water-dispersible granules include, e.g., formetanate hydrochloride, omite, profenofos, dimethoate, Dikar ®, ethion, dinocap, dicofol, amitraz, oxythioquinox, cyhexatin, fenbutatinoxide, oxamyl and phosalone.

The chemical names of the above nematicides and miticides are set forth, e.g., in the Farm Chemicals Handbook '87.

Representative safeners (antidotes) for use with herbicides which are specifically contemplated as being suitable for use in the water-dispersible granules of this invention include, e.g., 5-thiazolecarboxylic acid, 2-chloro-4-(trifluoromethyl),(phenylmethyl) ester, (common name "flurazole"), N-$\alpha,\alpha$-dichloroacetyl-1-oxa-4-azaspiro [4,5] decane (common name "AD-67"), N-$\alpha,\alpha$-dichloroacetyl-N,N-diallyl acetamide (common name "R25788"), N-$\alpha,\alpha$-dichloroacetyl-2,2-dimethyl-1,3-oxazolidine, N-$\alpha,\alpha$-dichloroacetyl-2,2,5-trimethyl-1,3-oxazolidine (common name "R29148"), $\alpha$-[(cyanomethoxy)imino]benzenacetonitrile, $\alpha$-[(1,3-dioxypyran-2-yl-methoxy)-imino] benzenacetonitrile, ethanone; 2,2-dichloro-1-(1,2,3,4-tetrahydro-1-methyl-2-isoquinolyl)-, and the like.

Representative plant growth regulants contemplated herein primarily for use as the non-encapsulated component in water-dispersible granules include, but are not limited to the following (chemical names found, e.g., in Farm Chemicals Handbook '87, unless otherwise indicated):

| | |
|---|---|
| Chlormequat chloride | Calcium arsenate |
| Diaminozide | Ethofumesate |
| Ancymidol | Dikegulac socium |
| Ethephon | XE 1019 |
| Maleic hydrazide | Flurprimidol[1] |
| Mefluidide | Paclobutrazol |
| Fluridamide[1] | Sodium sesqui salt |
| EPTC | of glyphosate[2] |
| Sulfometuron methyl | Amidichlor[3] |

[1]Plant Growth Regulating Chemicals, Vol. 1 (1983), Ed. L. G. Nickell, Chemical Rubber Co. Press
[2]Monsanto Company technical brochure
[3]$\alpha$-chloro-2,6'-diethyl-N-(acetamidomethyl) acetanilide The water-dispersible granules of this invention may comprise mixtures of an encapsulated pesticide and a non-encapsulated safener, or mixture of safeners e.g., amidochlor and/or paclobutrazol.

The encapsulated water-insoluble pesticide need not consist of only one type, but may be a combination of two or more various types of water-insoluble pesticides; e.g., such a combination may be one active herbicide with another active herbicide or an active herbicide or any other type of biocide or growth regulator, safener and/or an active insecticide. Higher melting solids need be solubilized within a second liquid active ingredient in order to be microencapsulated. Micro-encapsulation of higher melting solids is restricted more by the solubility of the solid in the liquid at encapsulation temperatures.

The above specifically-mentioned compounds are intended merely as representative of the types of compounds which may be used as the encapsulated or non-encapsulated component of the present water-dispersible granules. However, it is expressly contemplated that many other similar and analogous compounds known and described in the prior art for pesticidal or plant growth regulating purposes are suitably used as the encapsulated component. For example, other herbicidally useful acetanilide compounds are described in U.S. Pat. Nos. 3,442,945, 3,547,620, 3,830,841, 3,901,7685 and 4,517,011. The acetanilide compounds of U.S. Pat. No. 3,829,306 are useful as plant growth regulants.

Herbicidally-useful thiocarbamate compounds amenable to formulation as the water-dispersible granules of this invention include those disclosed in U.S. Pat. Nos. 2,913,327, 3,330,643 and 3,330,821.

Various other pyridine derivatives (in addition to and similar to those exemplified above) within the purview of this invention include those disclosed and claimed in copending U.S. Ser. No. 602,021, filed Apr. 24, 1984. Various embodiments of the compounds recited in that case include thioester and thioimidate derivatives of pyridine dicarboxylic acid esters.

Particularly useful other herbicidal pyridine derivatives include the cyclic imidate derivatives of pyridine dicarboxylic acid esters disclosed and claimed in copending U.S. Ser. No. 012,930, filed Feb. 9, 1987, and the pyrazole amide derivatives of pyridine dicarboxylates disclosed and claimed in copending U.S. Ser. No. 012,925, filed Feb. 9, 1987.

Other pyrazole derivatives suitable for use in the water-dispersible granules of this invention include the compounds disclosed in U.S. Pat. No. 4,298,749 and structurally-similar homologs, isomers and analogs thereof.

Another generic class of agrichemically-useful compounds specifically contemplated and preferred for use in the water-dispersible granules of this invention include N-phosphonomethyl glycine and the water-soluble salts and esters thereof, particularly the mono-alkali metal and mono-ammonium salts of glyphosate. Compounds further representative of this class of compounds are herbicidally-active compounds disclosed in U.S. Pat. Nos. 3,455,675, 3,799,758, 3,977,860, 3,868,407, 4,315,765, 4,397,676 and 4,405,531.

Other glyphosate derivatives useful as either herbicides or plant growth regulators for which the water-dispersible granule formulations of this invention are contemplated are disclosed in U.S. Pat. Nos. 4,159,901 and 4,140,513. Yet other derivatives of N-phosphonomethyl glycine contemplated herein as suitable for formulation as water-dispersible granules and used as plant growth regulants are disclosed in the following U.S. Pat. Nos.: 3,556,762, 3,850,608, 3,853,530 and 3,988,142.

It is within the purview of this invention to formulate water-dispersible granules of herbicidal compositions safened with a great variety of safeners. It is thus contemplated that in addition to the above-mentioned safeners, other suitable compounds include the $\alpha,\alpha$-dichloroacetyl-N,N-disubstituted acetamides used as safeners for, particularly, thiolcarbamate and acetanilide herbicides as disclosed in the following U.S. Pat. Nos.: 3,989,503, 4,124,372, 4,137,070, 4,021,224, 4,415,353, 4,392,884, 4,124,376 and 4,256,481.

Other compounds structurally similar to the above-mentioned flurazole safener contemplated for use herein are those 2,4-disubstituted-5-thiazolecarboxylic acids and derivatives thereof disclosed in U.S. Pat. No. 4,199,506.

Additional compounds structurally similar to the above-mentioned benzeneacetonitrile derivatives contemplated for use as safeners herein are those disclosed in U.S. Pat. Nos. 4,070,389, 4,152,137 and 4,269,775.

It is, therefore, within the purview of this invention that the present unique water-dispersible granules may be formulated from a great variety of compounds which are amenable for use as the encapsulated or the non-encapsulated component Accordingly, the compounds disclosed in the above-mentioned patents and patent applications are incorporated herein by reference to those patents and patent applications.

It will be readily understood by those skilled in the art that some aqueous suspension feedstocks of the encapsulated and non-encapsulated components will by their nature and composition be more difficult to dehydrate or dry from the aqueous suspension to the water-dispersible granule. Thus, e.g., the di-and tri-alkali metal and ammonium salts of glyphosate and certain alkylamino salts of glyphosate are more hygroscopic than the mono-salts, hence, dry with much more difficulty in a spray drying operation. Accordingly, such difficultly-driable feedstocks are less preferred embodiments of the invention, although improvements in drying techniques are expected.

Mention is made of U.S. Pat. No. 4,440,562 which is directed to a herbicidal emulsion of alachlor and the isopropylamine salt of glyphosate. While the emulsion of the '562 patent is an effective herbicide, certain shortcomings associated with that type of formulation relate to packaging disposal, and shelf-storage drawbacks, a certain measure of antagonism between the active ingredients and volatility losses. Thus, the plastic containers are more costly than paper or plastic bags and have to be disposed of (a cost and disposal problem) and the storage-stability of an emulsion is generally less than that of water-dispersible granules. Significantly, "wet" pesticidal formulations commonly exhibit volatility losses, particularly in "no-till" or "minimum-till" situations. In contrast, water-dispersible granules substantially reduce and/or eliminate the foregoing disadvantages of liquid formulations.

In bulk form, the water-dispersible granules of this invention comprise a collection of aggregates of microcapsules of the water-insoluble pesticide or plant growth regulant component, particles of the non-encapsulated component, formulation adjuvants and a small amount of water. This collection of granules is free-flowing, non-dusting and readily dispersible in aqueous media.

In the interfacial condensation encapsulation process used herein, the water-insoluble pesticide containing the first shell wall monomer dissolved therein comprises the organic or discontinuous phase liquid. The water-immiscible pesticide acts as the solvent for the first shell wall monomer thus avoiding the use of other water-immiscible organic solvents and allowing for a concentrated amount of water-insoluble pesticide in the final encapsulated product. The water-insoluble pesticide and first shell wall component are pre-mixed to obtain a homogeneous discontinuous phase liquid before addition to, and emulsification in, the aqueous phase to form the oil-in-water emulsion.

The concentration of water-insoluble pesticide initially present in the discontinuous phase liquid should be sufficient to provide at least about 300 grams of water-insoluble pesticide per liter of aqueous suspension. However, this is by no means limiting and a greater amount can be used. In practical operation, as will be recognized by those skilled in the art, the use of extremely high concentrations of water-insoluble pesticide will result in very thick suspensions of microcapsules. In general, the concentration of water-insoluble pesticide will range from about 400 grams to about 700 grams per liter of aqueous suspension. The preferred range is from about 480 grams to about 650 grams per liter of aqueous suspension.

The term "first shell wall monomer" refers to a material or mixture of materials which is soluble in the material to be encapsulated and which is capable of reacting with the second shell wall monomer to form a polymeric shell wall about the material to be encapsulated. As previously stated, the material to be encapsulated together with the first shell wall monomer constitute the discontinuous or organic phase liquid.

The term "second shell wall monomer", as used herein, refers to a water soluble material, i.e., a material which is soluble in the aqueous phase liquid and which will react with the first shell wall monomer to form a polycondensate shell wall about the material to be encapsulated. Table 1 illustrates various types of polycondensate shell walls formed when various first and second shell wall monomers are utilized in the process of encapsulation described herein:

TABLE 1

| First Shell Wall Component | Second Shell Wall Component | Polymeric Shell Wall |
|---|---|---|
| Diacid or Polyacid Chlorides | Diamine or Polyamine | Polyamide |
| Dichloroformates or Polychloroformates | Diamine or Polyamine | Polyurethane |
| Diisocyanates or Polyisocyanates | Diols or Polyols | Polyurethane |
| Disulfonyl or Polysulfonyl Chlorides | Diamine or Polyamine | Polysulfonamide |
| Diisocyanates or Polyisocyanate | Diamine or Polyamine | Polyurea |
| Diacid or Polyacid Chlorides | Diols or Polyols | Polyester |
| Dichloroformates or Polychloroformates | Diols or Polyols | Polycarbonate |

Examples of suitable difunctional, acid-derived shell wall monomers are sebacoyl chloride, ethylene bischloroformate, phosgene, terephthaloyl chloride, adipoyl chloride, azelaoyl chloride (azelaic acid chloride), dodecanedioic acid chloride, dimer acid chloride, and 1,3-benzenesulfonyl dichloride. Polyfunctional compounds of this type are exemplified by trimesoyl chloride, 1,2,4,5 benzene tetracid chloride, 1,3,5 benzene trisulfonyl chloride, trimer acid chloride, citric acid chloride, and 1,3,5 benzene trischloroformate. Intermediates similarly useful in the organic or discontinuous phase also include diisocyanates and polyisocyanates, for example, toluene diisocyanate, hexamethylene diisocyanate, methylene diphenylisocyanate and polymethylene polyphenylisocyanate. Preferred are the last-named polyisocyanates, represented by commercially-available polymethylene polyphenylisocyanates such as PAPI ® and PAPI-135 ® (registered trademarks of the Upjohn Company) and Mondur-MR ® (registered trademark of Mobay Chemical Company).

Examples of suitable diols for use as intermediates in the aqueous phase are bisphenol A [2,2 bis-(p,p'-dihydroxy diphenyl)propane], hydroquinone, resorcinol, catechol and various glycols such as ethylene glycol, pentanediol, hexanediol, dodecanediol, 1,4-butanediol and the like. Polyfunctional alcohols of this character, e.g., triols, are exemplified by pyrogallol (1,2,3-benzenetriol), phloroglucinol dihydrate, pentaerythritol, trimethylolpropane, 1,4,9, 10-tetrahydroxyanthracene, 3,4-dihydroxyanthranol, diresorcinol and tetrahydroxyquinone.

Instances of suitable diamines and polyamines, usually selected as water soluble per se or in water soluble salt form, where such reactant is to be included in the aqueous phase, are polymethylene diamines, phenylene diamine, toluene diamine, diethylene triamine and piperazine. Amines which are effective as polyfunctional reactants, are, e.g., 1,3,5-benzene triamine trihydrochloride, 2,4,6-triamino toluene trihydrochloride, polyethylene imine, 1,3,6-triaminonaphthalene, 3,4,5-triamino-1,2,4-triazole, malamine, and 2,4,5,8-tetramino anthraquinone. Amines which have a functionality greater than 2 but less than 3 and which may provide a degree of cross-linking in the shell wall are polyalkylene polyamines, e.g., tetraethylene pentamine, pentaethylene hexamine, and the like.

Particularly suitable amines are the polyfunctional amines which are capable of reacting with polymethylene polyphenylisocyanate to form a polyurea shell wall. The polyfunctional amines should be water soluble salt form. The usable polyfunctional amines can be selected from a wide range of such materials. Suitable examples of polyfunctional amines which may be used in this invention include, but are by no means limited to the following: ethylene diamine, propylene diamine, isopropylene diamine, hexamethylene diamine, toluene diamine, ethene diamine, triethylene tetraamine, tetraethylene pentamine, pentaethylene hexamine, diethylene triamine, bis-hexamethylene triamine and the like. The amines may be used alone or in combination with each other, preferably in combination with 1,6-hexamethylene diamine (HMDA). 1,6-hexamethylene diamine is preferred for use in the process of the present invention.

The first shell wall monomer and the second shell wall monomer form the shell wall which surrounds or encapsulates the water-insoluble pesticide. The shell wall content of the capsules may vary from about 5 percent to about 30 percent, preferably 6 to 20 percent and most preferably 7–10 percent by weight of the water-insoluble pesticide.

The amount of first shell wall monomer and second shell wall monomer to be used in the process is determined by the percent shell wall content produced. Generally, there will be present from about 3.5 percent to about 21.0 percent first shell wall monomer, and from about 1.5 percent to about 9.0 percent second shell wall monomer, relative to the weight of the water-insoluble pesticide present in the reaction.

In order to obtain encapsulation of from 400 to 700 grams per liter of water-immiscible pesticide it is necessary to use the specific emulsifiers described below to achieve a stable oil-in-water emulsion. The emulsifying agents, which are advantageously used in encapsulating concentrated amounts of water-insoluble pesticide are:

1. The water-soluble salts of lignin sulfonate, e.g., the sodium, potassium, magnesium, calcium or ammonium salts of lignin sulfonate. The sodium salt of lignin sulfonate is preferred for use herein. Any commercially available lignin sulfonate salt which does not contain added surfactant, may be conveniently employed herein. Commercially available lignin sulfonate emulsifiers which may be mentioned are: Treax ®, LTS, LTK and LTM, respectively, the potassium, magnesium and sodium salts of lignosulfonate (50% aqueous solutions), Scott Paper Co., Forest Chemical Products; Marasperse CR ® and Marasperse CBOS-3 ®, sodium lignosulfonate, and Marasperse C21 ®, calcium sulfonate, Reed Lignin Co., Polyfon O ®, Polyfon T ®, Reax 88B ®, Reax 85B ®, sodium salts of lignin sulfonate, Westvaco Polychemicals.

2. Sulfonated naphthalene-formaldehyde condensates having the formula:

$$\left[ \begin{array}{c} \phantom{X} \\ \text{SO}_3^- \text{M}^+ \end{array} \text{naphthalene} - \text{CH}_2 - \right]_n$$

where n is 2 or 3 and M is an alkali or alkaline earth metal cation. Commercially available examples which may be mentioned are Tamol ® SN, the sodium salt of condensed naphthalene sulfonic acid manufactured by Rohm and Haas Company, Philadelphia, Pa. 19105; "Daxad" 11G, 16, 17 and 19, the sodium salt of polymerized alkyl naphthalene sulfonic acid, manufactured by W. R. Grace and Company, Organic Chemicals Division, Lexington, Me. 02173;"Blancol" N, the sodium salt of sulfonated naphthalene-formaldehyde condensate manufactured by GAF Corporation, Chemical Products, 140 West 51st Street, New York, N.Y. 10020.

3. Sulfonated polystyrenes with molecular weights above about 1,000 and an equivalent weight per acid group between about 150 and about 750, as for example, sulfonated polystyrenes of the formula:

$$\left[ \begin{array}{c} -\text{CH} - \text{CH}_2 - \\ | \\ \text{C}_6\text{H}_4 \\ | \\ \text{SO}_3^- \text{M}^+ \end{array} \right]_n$$

where n is greater than 5 and M is an alkali or alkaline earth metal cation. Commercially available examples of such materials are Versta ® TL 500 and TL 600, sulfonated polystyrene manufactured by National Starch and Chemical Corporation, 10 Findeine Avenue, Bridgewater, N.J. 08807.

4. Water-soluble alkylated polyvinylpyrrolidone (PVP) polymer; e.g., Ganex ® P-904 which has an average molecular weight of 16,000 and which is a 10% weight butylated-PVP polymer manufactured by GAF Corp., Chemical Products, 140 W. 51st St., New York, N.Y. 10020. U.S. Pat. Nos. 3,417,054 and 3,423,381 describe the preparation of such alkylated PVP polymers. Unalkylated PVP polymers which may be mixed with alkylated PVP polymers to produce a water-soluble PVP mixture which will form a stable oil-in-water emulsion under the process conditions described herein are Ganex ® K-15, K-30 and K-90 having average molecular weights of 10,000, 40,000 and 360,000 respectively; these materials are available from GAF Corporation.

The range of emulsifier concentration found most acceptable in the system will vary from about 0.5 percent to about 15 percent and preferably from about 2 percent to about 6 percent, based on the weight of the water-immiscible material and most preferably at from about 2.0 to about 4.0 percent and most preferably at a concentrate of 2 percent relative to the weight of the water-immiscible pesticide.

In the practice of the encapsulation process described herein, the temperature should be maintained above the melting point of the water-insoluble pesticide material but below the temperature wherein the discontinuous phase monomer will begin to hydrolyze or otherwise break down. For example, where it is desired to encapsulate a solid herbicide, it will be necessary to heat the herbicide to its molten state. Alachlor herbicide, for example, melts at 39.5° C. to 41.5° C. and the temperature of the process should accordingly be maintained in the 42°–45° C. range.

The agitation employed to establish the dispersion of discontinuous phase droplets in the aqueous phase may be supplied by any means capable of providing suitably high shear, that is, any variable shear mixing apparatus, e.g., a blender, a Brinkman Polytron homogenizer, Ross Model 100L homogenizer, Tekmar, and the like, can be usefully employed to provide the desired agitation.

The particle size of the microcapsules and other pesticide ingredients will range from about 1 micron up to about 100 microns in size. From about 1 to about 10 microns is an optimum range. From about 5 to about 50 microns is satisfactory for spray drying.

The aqueous suspension of microcapsules containing the water-insoluble pesticide, the non-encapsulated pesticide and suspension and agglomeration adjuvants form the "feed stock" for subsequent spray drying. Droplets of feed stock are spray dried in a spray dry tower to produce the water-dispersible granules of the invention. The droplets are formed using conventional spray dry nozzles. The nozzle has two primary functions:

1. To atomize or break up the aqueous suspension into droplets of the desired size, and
2. To distribute these droplets in a specific pattern in the tower.

An appropriate nozzle is used to atomize the aqueous suspension in a spray drying tower where drying occurs. Generally, single-fluid hollow-cone nozzles of the type previously described are preferred as they produce large uniform droplets. As water is removed from each droplet an aggregate is formed consisting essentially of many small microcapsules associated together, with a fine layer of suspension adjuvant homogeneously interspersed between each micro-capsule. The entire drying process may occur in the spray dry tower; however, to avoid the possibility of overheating of the aggregate which will result in the formation of a water-dispersible granule which will not dissociate when added to water; secondary drying may advantageously be used in the final stage.

Secondary drying is most advantageously accomplished by use of a vibra-fluidized bed for second stage drying. The water-dispersible granule product is dried in the spray dry tower to a moisture level of about 6% to about 10% by weight. The granules are collected from the tower and passed through fluid-bed dryers to bring the moisture level of the water-dispersible granules to no more than 8.0% by weight and, preferably, about 4% and still more preferably about 1.0% to about 2.0% by weight.

In order to produce a water-dispersible granule having the particle size range described herein, it is necessary to produce as large and uniform a droplet as possible from a given nozzle orifice. The nozzle should be chosen so as to produce large uniform particles over a narrow distribution range. Larger droplets can be expected as the orifice size is increased at a given pressure. In general, lower pressure and higher feedstock viscosity will increase particle size. In general, from $1379-2758 \times 10^3$ N/m² will be required to produce the large uniform droplets; from $1379-2069 \times 10^3$ N/m² may be used with about $1379 \times 10^3$ N/m² found to be optimal for liquids in the 800–1200×10$^{-3}$ N s/m$^2$ viscosity range often encountered for feedstocks described herein.

Multiple nozzles can be used to atomize the droplets of aqueous suspension into the spray tower. However, as will be recognized by one skilled in the art, the number of nozzles used will be limited by the drying capacity attainable in the tower.

Spray-dry nozzles found to be useful herein are single fluid, hollow-cone nozzles. A single-fluid, solid-cone nozzle may also be used herein and this nozzle is similar in design to the swirl-chamber nozzle except that a special core or axial jet fills the center of the conical pattern. The resulting full-volumetric coverage enhances rates of mass and heat transfer between the spray liquid and gas passing through the cone. The included spray angle ranges from 30°–120°.

The above and other types of atomization devices are known and are commercially available as are fan-spray nozzles and disk atomizers. However, preferred for use herein are the single fluid, hollow-cone nozzles previously described.

Single-fluid nozzles are preferred over two fluid atomizers which are pneumatically operated to provide small atomized particles at low pressure. Single fluid nozzles are particularly useful for spraying high viscosity materials and for the formation of larger droplets which, when dried produce large aggregates. The larger volume and greater density of droplets formed from single-fluid nozzles requires longer residence time in the dispersing air flow allowing for more efficient drying in the spray tower. The droplets formed are homogeneous and produce a narrow aggregate size distribution particularly when hollow-cone nozzles are employed to direct the spray from the nozzle at radial velocities. Size uniformity is important in providing the best product performance compromise by avoiding dust from small particles while still providing particles small enough to rapidly disperse in water. Size uniformity is also important in the drying process to provide uniform drying of individual particles to assure their rapid reconstitution in water.

The best results relative to product rate and quality by use of a mixed-flow fountain spray (wherein product feed into spray tower is in a direction opposite to the drying air stream) are achieved using a spray nozzle which produces a spray angle of from about 46° to 60° at pressure of about 1379–1896 N/m$^2$. Such nozzles produce atomization and projection of the aqueous suspension far enough up into the spray drying chamber to take advantage of available drying capacity. Angles greater than about 60° "fan out" and do not project high enough into the tower to take advantage of the maximum residence time and drying capacity of the tower. This usually causes "wetting" or wall buildup in the tower. Similar results may be obtained using a co-current spray-dry mode.

The spray dryer is a large, usually vertical, chamber through which a hot gas is blown, and into which the aqueous suspension is sprayed by a suitable nozzle atomizer to form droplets. All droplets must be dried until no longer sticky, before they strike the chamber wall; therefore, the largest drop produced by a given nozzle determines the size of the spray chamber, and chamber shape is fixed by spray pattern. A spray dryer may be cocurrent, countercurrent, or mixed flow. Counter-current tends to expose the driest particle to the hottest temperature, making it unsuitable for many of the heat sensitive systems described herein. Laminar flow cocurrent dryers are advantageously used for heat sensitive materials to permit the use of higher inlet and outlet temperatures. Typical inlet temperatures are within the range of about 255°–315° C. Outlet temperatures are within the range of about 120° to 150° C.

The inlet temperature in the mixed flow drying modes at the top of the spray tower should be from about 200° C. to about 275° C. The outlet temperature coming off the tower should be from about 90° C. to about 135° C. Temperatures in excess of these may cause fusing of particles in the agglomerate which is detrimental to spontaneity and redispersion of the water-dispersible granule in water. The temperature of the water-dispersible granule coming out of the tower should be below a temperature at which the shell wall would fuse, e.g., in the case of alachlor about 55°–75° C.

Product coming out of the tower contains 7–9% moisture which requires secondary drying to reduce the moisture to from 2–4%.

In order to obtain an essentially spherical water-dispersible granule (aggregate) which is from about 180 to about 420 microns in diameter, it has been found to be advantageous to use a mix flow a spray dry mode with a tower having an inside diameter and cylindrical drying chambers from about 3.66 m to about 12.19 m and with a 30°–60° collection cone.

The optimum pressure for operating the spray nozzle is a range of from about 1035–2069×10$^3$ N/m$^2$, preferably from about 1379 to about 2069, and more preferably from about 1724 to about 1896×10$^3$ N/m$^2$.

The following examples illustrate specific embodiments of the invention. As will be recognized by one skilled in the art, these examples are illustrative and are not meant to be limiting.

EXAMPLE 1

This example describes the encapsulation of 2-chloro-2′,6′-diethyl-N-(methoxymethyl) acetanilide (common name "alachlor") herbicide in a polyurea shell wall, followed by admixture with 2-chloro-4-ethylamino-6-isopropyl amino-1,3,5-triazine (common name "atrazine") to form the aqueous feedstock with is then dried by spray drying, as described in Example 2.

The process described in this example was followed to prepare the feedstock for two formulations (A and B) containing different concentrations of alachlor and atrazine (herbicidal compounds) and variations in adjuvant composition.

The aqueous suspension (feedstock) of encapsulated alachlor was produced in two consecutive stages. The first stage, encapsulation, was a continuous process; the second stage, addition of a second, non-encapsulated herbicide and formulation ingredients, was accomplished post-encapsulation in a batch mode.

A continuous stream of molten alachlor and a polymethylene polyphenylisocyanate (PAPI), the first shell wall monomer, were fed together and mixed using a static mixer. The combined stream formed the discontinuous phase liquid which was added to a stream of aqueous (continuous phase) liquid containing water and sodium lignin sulfonate emulsifier (Reax 88B) wherein an oil-in-water emulsion was formed using high shear (Tekmar Dispax homogenizer). Into the stream of the emulsion was fed a continuous stream of aqueous hexamethylene diamine (HMD), the second shell wall monomer. The combined stream was immediately passed through a static mixer, whereupon the first and second shell wall monomers reacted to form a solid polyurea film about the droplets of alachlor.

The aqueous suspension which is composed of microcapsules (1–50 microns in diameter) suspended in water containing the lignin sulfonate emulsifier) was fed to a holding tank where atrazine and the formulation adjuvants used as suspension agents in the aqueous suspension and/or subsequently as "agglomeration adjuvants", i.e., binders/separators, anti-caking, etc. agents in the dried, water-dispersible granules, were added to form the final feedstock which was sprayed in the spray tower. The finished feedstock was filtered through a 100 mesh high-speed vibration filter to remove any foreign material. The feedstock for the two formulations has the compositions:

| Ingredient | Feedstock (Percent by Weight) | |
|---|---|---|
| | A | B |
| Alachlor (94%) | 29.92 | 29.36 |
| Atrazine (95%) | 17.96 | 17.63 |
| HMD (43%) | 2.13 | 2.09 |
| Papi | 2.09 | 2.05 |
| Reax 88B | 0.60 | 0.60 |
| NaCl | 1.60 | 1.60 |
| CaCl$_2$ | 3.20 | 3.20 |
| PVP-K-15 | 0.50 | 0.50 |
| Duponol C | — | 2.40 |
| Igepon T-77 | 2.40 | — |
| Petro Ag Spec | 2.40 | 2.40 |
| Hisill 233 | 2.40 | 2.40 |
| Barden Clay | 0.60 | 1.20 |
| Sag 47 | 0.20 | 0.20 |
| Water | 34.00 | 34.37 |
| | 100.00 | 100.00 |

Feedstock A has a solids content of 64.77% and Feedstock B contained 64.43% solids. The alachlor/atrazine weight ratio was about 1.66 to 1.0 for both formulations.

EXAMPLE 2

The feedstocks of Example 1 were used to prepare Formulations A and B, i.e., dry, free-flowing water-dispersible granules containing microencapsulated alachlor and non-encapsulated particles of atrazine as the herbicidal content of the granules.

The feedstocks for Formulations A and B were separately fed to a spray tower for the drying and the granules-agglomeration procedure.

The spray tower was a 15.24 m tower having a verticle height of 7.62 m, a cone height of 7.62 m and a diameter of 6.71 m. The spray drying mode was mixed-flow. The blower speed was constant at approximately 155.74 m$^3$/min. Air was passed directly through a gas fired furnace and discharged from the center at the top of the tower. Excellent air turbulence was achieved relative to the position of the nozzles in the tower. A Spray Systems, single fluid, hollow-cone nozzle with an orifice/core combination of B-48+B-640 was used. Nozzle pressure was from about 1379 to 1724×10$^3$ N/m$^2$. Three nozzles were used and were directed toward top of tower, counter-current to the hot air flow. Nozzle tips were approximately 10.67 m from the top of the tower and were located at the lower center, with nozzles 0.61 m off center apart from each other at a 120° angle. The inlet temperature ranged from about 232°–300° C. with 232°–260° C. being optimum. The outlet temperature ranged from about 122°–170° C. with 122°–135° C. being optimum. The temperature of the product coming from the tower was about 60° C. to about 77° C.

The compositions of the spray-dried granules of Formulations A and B were as follows:

| Ingredient | Formulation (Percent by Weight) | |
|---|---|---|
| | A | B |
| Alachlor (94%) | 45.45 | 44.33 |
| Atrazine (95%) | 26.74 | 26.62 |
| Polyurea Shell Wall | 4.54 | 4.43 |
| Reax 88B | 0.91 | 0.90 |
| NaCl | 2.43 | 2.42 |
| CaCl$_2$ | 4.86 | 4.84 |
| PVP-K-15 | 0.76 | 0.75 |
| Duponol C | — | 3.62 |
| Igepon T-77 | 3.65 | — |
| Petro Ag Spec | 3.65 | 3.62 |
| Hisill 233 | 3.65 | 3.62 |
| Barden Clay | 0.91 | 1.81 |
| Sag 47 | 0.30 | 0.30 |
| Water | 2.15 | 2.74 |
| | 100.00 | 100.00 |

The product characteristics of the spray-dried water-dispersible granules are shown in Table I.

TABLE I

PRODUCT CHARACTERISTICS FOR FORMULATIONS A AND B

| Formulation | Product Moisture (Wt %) | Residue Bulk 200 Wet Sieve (Wt %) | Spon. | Wetting | Granule Size Dist. Cumm. (% on Screen/Pan)* Mesh | | | | | Bulk Density (Kg/m$^3$) |
|---|---|---|---|---|---|---|---|---|---|---|
| | | | | | +35 | +60 | +80 | +100 | PAN | |
| A | 1.0 | 0.4 | EX | EX | 24 | 90.7 | 99.3 | 99.9 | 0.1 | 59.3 |
| B | 3.0 | 1.0 | EX | EX | 37 | 84 | 97 | 99.2 | 0.8 | 57.7 |

Ex = Excellent
V.G. = Very Good
Trace = <0.1%
Spon. = Spontaniety
*Mesh Size
35 mesh = 500 microns
60 mesh = 250 microns
80 mesh = 180 microns
100 mesh = 150 microns
PAN mesh = 150 <microns

EXAMPLE 3

Following the procedures described in Examples 1 and 2, water-dispersible granules of Formulation C below were prepared having the following composition:

| FORMULATION C | |
|---|---|
| Ingredients | Percent By Weight |
| Alachlor (94%) | 44.60 |
| Atrazine (95%) | 26.80 |
| Polyurea Shell Wall | 4.46 |
| Reax 88B | 0.94 |
| PVP K-15 | 0.79 |
| NaCl | 2.40 |
| CaCl$_2$ | 4.84 |
| Duponol C | 3.54 |
| Petro Ag Spec | 3.54 |
| Hisill 233 | 3.54 |
| Barden Clay | 1.70 |
| Sag 47 | 0.32 |
| Water | 2.50 |
| TOTAL: | 100.00 |

Formulation C has the following product characteristics:

| Bulk Density | 49.2 Kg/m$^3$ |
|---|---|
| Flow Properties "D.F." | Dry, Free Flowing Non-dusting |
| Product Moisture | 2.5% |
| Spontaneity 10° C. Tap Water | Excellent <10 sec complete dispersion |
| Wetting 10° C. Tap Water | Excellent |
| % Residue 200 screcal "Wet Sieve" | <0.1% |
| Aggregate Size Distr.[1] | % Retained |
| +35 mesh 500 microns | 32.0 |
| +60 mesh 250 microns | 57.5 |
| +80 mesh 180 micons | 9.2 |
| +100 mesh 150 microns | 1.2 |
| on pan < 150 microns | 0.1 |
| % on +60 mesh[2] | 89.5 |
| +35/+60 mesh ratio | 1:1.8 |

[1]not cumulative
[2]cumulative

EXAMPLE 4

In a manner similar to that described in the preceding examples, water-dispersible granules of micro-encapsulated alachlor admixed with non-encapsulated atrazine were prepared, having the component content shown in Formulations D and E.

| | Formulation (Percent by Weight) | |
|---|---|---|
| Ingredient | D | E |
| Alachlor (94%) | 44.54 | 44.50 |
| Atrazine (95%) | 26.77 | 26.23 |
| Polyurea Shell Wall | 4.45 | 4.45 |
| Reax 88B | 0.93 | 0.90 |
| Polypylene Glycol | 2.12 | — |
| PVP-K-15 | — | 0.80 |
| NaCl | 2.43 | 4.51 |
| CaCl$_2$ | 5.00 | — |
| Duponol C | — | 3.20 |
| Igepon T-77 | 3.53 | — |
| Witconate (90%) | — | 7.21 |
| Petro Ag Spec | 3.53 | 3.20 |
| Hisill 233 | 3.53 | 3.70 |
| Barden Clay | 1.78 | — |
| Sag 47 | 0.32 | 0.30 |
| Water | 1.00 | 1.00 |
| | 100.00 | 100.00 |

Formulation D exhibited some caking in storage, poorer spontaneity and excessive residue (i.e., >2% by wt.) in the wet screen test than Formulation E. Polyvinylpyrrolidone is a better anti-caking aid than propylene glycol and Duponol C provides better reconstitution properties than Igepon T-77.

EXAMPLE 5

The process described in this example was followed to prepare a feedstock (Feedstock F) containing alachlor and imazaquin (active ingredient in SCEPTER ® herbicide), plus formulation adjuvants.

The aqueous suspension (feedstock) of herbicides and formulation adjuvants was produced in two stages. The first stage, encapsulation, was a continuous process; the second stage, addition of a second, non-encapsulated herbicide and formulation ingredients, was accomplished post-encapsulation in a batch mode.

A continuous stream of molten alachlor and a polymethylene polyphenylisocyanate (PAPI) the first shell wall monomer were fed together and mixed using a static mixer. The combined streams formed the discontinuous phase liquid which was added to a stream of aqueous continuous phase liquid containing water and sodium lignin sulfonate emulsifier (REAX 88B) wherein an oil-in-water emulsion was formed using high shear (Tekmar Dispax homogenizer). Into the stream of the emulsion was fed a continuous stream of aqueous hexamethylene diamine (HMD), the second shell wall monomer. The combined stream was immediately passed through a static mixer, whereupon the first and second shell wall monomers reacted to form a solid polyurea film about the droplets of alachlor.

The aqueous suspension which is composed of microcapsules (1–50 microns in diameter) containing alachlor suspended in water containing the lignin sulfonate emulsifier was fed to a holding tank where imazaquin and the formulation adjuvants used as suspension agents in the aqueous suspension and/or subsequently as "agglomeration adjuvants", i.e., binders/separators, anti-caking, wetting, re-dispersion, etc. agents in the dried, water-dispersible granules, were added to form the final feedstock, which was spray dried in the spray tower as described in Example 6. The finished feedstock was filtered through a 100 mesh (150 micron) high-speed vibration filter to remove any foreign material. The feedstock for the formulation had the following composition.

| FEEDSTOCK F | |
|---|---|
| INGREDIENT | PERCENT BY WEIGHT |
| Alachlor (94.5%) | 44.72 |
| Imazaquin (94%) | 2.72 |
| HMD (43%) | 3.13 |
| PAPI | 3.13 |
| REAX 88B | 0.96 |
| Al$_2$ (SO$_4$)$_3$.18H$_2$O | 1.74 |
| (NH$_4$)$_2$ SO$_4$ | 3.45 |
| Witconate AOS (39%) | 3.53 |
| Water | 36.62 |
| TOTAL: | 100.00 |

The above formulation had a solids content of 59.47%. The alachlor: imazaquin ratio is 16:1.

EXAMPLE 6

The feedstock of Example 5 was fed to the spray tower for the drying and granules—agglomeration procedure.

The spray tower was a 15.24 m tower having a vertical height of 7.62 m, a cone height of 7.62 m and a diameter of 6.71 m. The spray-dry mode was mix-flow. The blower speed was constant at approximately 155.74 m$^3$/min.

Air was passed directly through a gas fired furnace and discharged from the center at the top of the tower. Excellent air turbulence was achieved relative to the position of the nozzles in the tower. A Spray Systems, single fluid, hollow-cone nozzle with an orifice/core combination of B-48+B-640 was used. Nozzle pressure was from about 1979 to 1724×10$^3$ N/m$^2$. Three nozzles were used and were directed toward top of tower, counter-current to the hot air flow. Nozzle tips were approximately 10.67 m from the top of the tower and were located at the lower center, with nozzles 0.61 m off center apart from each other at a 120° angle. The inlet temperature ranged from about 232°–300° C. with 232°–260° C. being optimum. The outlet temperature ranged from about 122°–170° C. with 122°–135° C. being optimum. The temperature of the product coming from the tower was about 60° C. to about 71° C.

The composition of the spray-dried granules of this example (Formulation F) was as follows:

| FORMULATION F | |
|---|---|
| INGREDIENT | PERCENT BY WEIGHT |
| Alachlor (94.5%) | 74.70 |
| Imazaquin (97%) | 4.54 |
| Polyurea shell wall | 7.47 |
| REAX 88B | 1.50 |
| Al$_2$(SO$_4$)$_3$.18H$_2$O | 2.91 |
| (NH$_4$)$_2$SO$_4$ | 5.76 |
| Witconate AOS | 2.30 |
| Water | 0.80 |
| TOTAL: | 100.00 |

The alachlor:imazaquin ratio is 16:1.

The product characteristics of the spray-dried water-dispersible granules of Formulation F are shown in Table II.

EXAMPLE 7

The process described in this example was followed to prepare an aqueous suspension feedstock (Feedstock G) containing microcapsules of encapsulated acetochlor herbicide and AD-67 (as safener for acetochlor) and particles of non-encapsulated atrazine, plus formulation adjuvants.

The aqueous suspension (feedstock) of encapsulated acetochlor plus AD-67 and non-encapsulated atrazine was produced in two stages. The first stage, encapsulation, was a continuous process. The second stage, additional of a non-encapsulated herbicide (atrazine) and formulation ingredients was accomplished post-encapsulation in a batch mode.

A continuous stream composed of AD-67 dissolved in hot (48° C.) acetochlor and a stream of polymethylene polyphenylisocyanate (PAPI), the first shell wall monomer, were fed together and mixed using a static mixer. The combined streams formed the discontinuous phase liquid which was added to a stream of aqueous continuous phase liquid containing water and sodium lignin sulfonate emulsifier (REAX 88B, while still maintaining a temperature at 48° C., wherein an oil-in-water emulsion was formed using high shear (Tekmar Dispax Homogenizer). Into the stream of the emulsion was fed a continuous stream of aqueous hexamethylene diamine (HMD), the second shell wall monomer. The combined stream was immediately passed through a static mixer, whereupon the first and second shell wall monomers react to form a solid polyurea film about the droplets containing acetochlor and AD-67, thus forming microcapsules thereof.

The aqueous suspension, composed of said microcapsules (1–50 microns in diameter) suspended in water containing the lignin sulfonate emulsifier, was fed to a holding tank where an aqueous slurry containing atrazine and the formulation adjuvants (used as suspension, re-dispersion, wetting, binders, separators, anti-caking agents, etc. in the feedstock and dried water-dispersible granules), was added to form the final feedstock which was spray dried in the spray tower. The feedstock for the formulation had the following composition.

| FEEDSTOCK G | |
|---|---|
| INGREDIENT | PERCENT BY WEIGHT |
| Acetochlor (93.3%) | 28.33 |
| Safener AD-67 (94%) | 2.83 |
| Atrazine (97.5%) | 16.31 |
| HMD (43%) | 1.98 |
| PAPI | 1.98 |
| REAX 88B | 0.50 |
| PVP K-15 | 0.40 |
| NaCl | 1.70 |
| CaCl$_2$ | 3.40 |
| Petro AG Special | 2.40 |
| DUPONOL C | 2.40 |
| HISILL 233 | 2.10 |
| Barden Clay | 1.05 |
| Water | 34.62 |
| TOTAL | 100.00 |

The above feedstock has a total solids content of 64.25%. Ratios of active ingredients were acetochlor:AD-67, 10:1 and acetochlor:atrazine, 1.66:1.

The above feedstock was fed to a spray tower for the drying and granules-agglomeration according to the same procedure described in Example 6.

Alternative embodiments of Example 7 include water-dispersible granules of microencapsulated acetochlor without a safener (in acetochlor-resistant crops where no safener is needed) and atrazine as the non-encapsulated herbicide.

The composition of the resulting spray-dried granules, designated as Formulation G, is as follows:

| FORMULATION G | |
|---|---|
| INGREDIENT | PERCENT BY WEIGHT |
| Acetochlor (93.3%) | 43.65 |
| Safener AD-67 (94%) | 4.36 |
| Atrazine (97.5%) | 25.13 |
| Polyurea shell wall | 4.37 |
| REAX 88B | 0.77 |
| PVP K-15 | 0.62 |
| NaCl | 2.62 |
| CaCl$_2$ | 5.24 |
| Petro AGS | 3.70 |
| DUPONOL C | 3.70 |
| Hisill 233 | 3.24 |
| Barden Clay | 1.62 |
| Water | 0.98 |
| TOTAL: | 100.00 |

Product characteristics of Formulation G are shown in Table II.

TABLE II
PRODUCT CHARACTERISTICS FOR FORMULATIONS F AND G

| Formulation | Product Moisture (Wt %) | Residue Bulk 200 Wet Sieve (Wt %) | Spon. | Wetting | Granule Size Dist. Cumm. (% on Screen/Pan)* Mesh | | | | | Bulk Density (Kg/m$^3$) |
|---|---|---|---|---|---|---|---|---|---|---|
| | | | | | +35 | +60 | +80 | +100 | PAN | |
| F | 1.0 | Trace | EX | V.G. | 67 | 82 | 91.2 | 98.2 | 1.8 | 48.1 |
| G | 1.0 | 0 | EX | EX | 18 | 80 | 95 | 98 | 2.0 | 54.5 |

Ex = Excellent
V.G. = Very Good
Trace = <0.1%
Spon. = Spontaniety
*Mesh Size
35 mesh = 500 microns
60 mesh = 250 microns
80 mesh = 180 microns
100 mesh = 150 microns
PAN mesh = 150 <microns

EXAMPLE 8

This example describes the encapsulation of alachlor herbicide in a polyurea shell wall, followed by admixture with, in separate formulations, an alkali metal salt of N-phosphonomethyl glycine (common name "glyphosate") to form the aqueous feedstock which is then dried by spray drying, as described in preceding examples.

The process described in this example was followed to prepare the feedstock for seven formulations (H-N) containing different concentrations of alachlor and a mono-sodium salt or mono-potassium salt of glyphosate (herbicidal compounds) and variations in adjuvant composition.

The aqueous suspension (feedstock) of encapsulated alachlor was produced in two consecutive stages. The first stage, encapsulation, was a continuous process; the second stage, addition of the water-soluble non-encapsulated salt of glyphosate herbicide and formulation ingredients, was accomplished post-encapsulation in a batch mode.

A continuous stream of molten alachlor and a polymethylene polyphenylisocyanate (PAPI), the first shell wall monomer, were fed together and mixed using a static mixer. The combined stream formed the discontinuous phase liquid which was added to a stream of aqueous (continuous phase) liquid containing water and naphthalene sulfonate (DAXAD 17) or sodium lignin sulfonate (Reax 88B) emulsifier wherein an oil-in-water emulsion was formed using high shear (Tekmar Dispax homogenizer). Into the stream of the emulsion was fed a continuous stream of aqueous hexamethylene diamine (HMD), the second shell wall monomer. The combined stream was immediately passed through a static mixer, whereupon the first and second shell wall monomers reacted to form a solid polyurea film about the droplets of alachlor.

The aqueous suspension which is composed of microcapsules (1–50 microns in diameter) suspended in water containing the emulsifier) was fed to a holding tank where the glyphosate salt and the formulation adjuvants used as suspension agents in the aqueous suspension and/or subsequently as "agglomeration adjuvants", i.e., binders/separators, anti-caking, etc. agents in the dried, water-dispersible granules, were added to form the final feedstock which was sprayed in the spray tower. The finished feedstock was filtered through a 100 mesh high-speed vibration filter to remove any foreign material. The feedstock for the seven formulations had the compositions:

| Ingredients | Feedstock (Percent by Weight) | | | | | | |
|---|---|---|---|---|---|---|---|
| | H | I | J | K | L | M | N |
| Alachlor (94%) | 33.88 | 33.88 | 31.86 | 28.34 | 35.00 | 33.12 | 27.53 |
| Polyurea Shell Wall | 3.39 | 3.39 | 3.19 | 2.83 | 3.50 | 3.31 | 2.75 |
| K Glyphosate | 16.09 | 16.09 | — | — | — | — | — |
| Na Glyphosate | — | — | 13.96 | 12.42 | 15.34 | 14.51 | 12.06 |
| Reax 88B | 0.68 | — | 0.64 | 0.57 | 0.70 | 0.66 | 0.55 |
| Daxad 17 | — | 0.68 | — | — | — | — | — |
| NaCl | — | — | 1.36 | 1.23 | 1.53 | 1.44 | — |
| (NH$_4$)$_2$SO$_4$ | — | — | — | — | — | — | 21.43 |
| Witconate AOS (100%) | 6.37 | 6.37 | 5.58* | 4.96* | 3.85* | 3.61* | 5.18 |
| Duponol C | — | — | 2.03 | 1.85 | 2.28 | 2.16 | — |
| Petro Ag Spec | — | — | 2.20 | 1.95 | 2.40 | 2.39 | — |
| SAG 47 | 0.33 | 0.33 | 0.11 | 0.11 | 0.13 | 0.11 | 0.27 |
| Hisill 233 | — | — | — | 2.66 | — | 3.11 | — |
| Water | 39.26 | 39.26 | 39.07 | 43.08 | 35.27 | 35.58 | 30.23 |
| | 100.00 | 100.00 | 100.00 | 100.00 | 100.00 | 100.00 | 100.00 |

*Theoretical - 5.99, 5.32, 6.58, 6.23, respectively, for Formulations J, K, L and M The alachlor/acid glyphosate (Na or K salt) weight ratio was about 2.5 to 1.0 for all formulations.

EXAMPLE 9

The feedstocks of Example 8 were used to prepare Formulations H-N, i.e., dry, free-flowing water-dispersible granules containing microencapsulated alachlor and non-encapsulated particles of the sodium or potassium salt of glyphosate as the herbicidal content of the granules The feedstocks for Formulations H-N were separately fed to a spray tower for the drying and the granules-agglomeration procedure.

The spray tower was a 15.24 m tower having a vertical height of 7.62 m, a cone height of 7.62 m and a diameter of 6.71 m. The spray drying mode was mixed-flow. The blower speed was constant at approximately 155.74 m³/min. Air was passed directly through a gas fired furnace and discharged from the center at the top of the tower. Excellent air turbulence was achieved relative to the position of the nozzles in the tower. A Spray Systems, single-fluid, hollow-cone nozzle with an orifice/core combination of B-48+B-640 was used. Nozzle pressure was about $2 \times 10^6$ N/m² (300 psi). Two nozzles were used and were directed toward top of tower, counter-current to the hot air flow. Nozzle tips were approximately 9.7 m from the top of the tower and were located at the lower center, with nozzles 0.4 m off center apart from each other at a 100° angle. The inlet temperature ranged from about 230°–280° C. with 240°–250° C. being optimum. The outlet temperature ranged from about 120°–180° C. with 140°–160° C. being optimum. The temperature of the product coming from the tower was about 60° C. to about 100° C.

The compositions of the spray-dried granules of Formulations H-N were as follows:

and non-encapsulated water-soluble ammonium salt of glyphosate.

In the first stage of the process, an aqueous suspension of alachlor was produced in the manner described in Example 8.

The aqueous suspension which is composed of microcapsules (1–50 microns in diameter) suspended in water containing the emulsifier) was fed to a holding tank where the ammonium glyphosate salt and formulation adjuvants (used as suspension agents in the aqueous suspension and/or subsequently as "agglomeration adjuvants", i.e., binders/separators, anticaking, etc. agents in the dried, water-dispersible granules) were added to form the final feedstock (Feedstock O), which was to be subsequently spray dried in the spray tower.

The finished feedstock was filtered through a 100 mesh screen to remove foreign material. Feedstock O had the following composition:

| FEEDSTOCK O | | |
|---|---|---|
| Ingredients | % By Weight | |
| Alachlor (94%) | 22.26 | (20.92 100% active) |
| Polyurea Shell Wall | 2.23 | |
| Glyphosate (90%; NH₄ Salt) | 9.34 | (8.4% Acid Equiv.) |

| | Formulation (Percent by Weight) | | | | | | |
|---|---|---|---|---|---|---|---|
| Ingredient | H | I | J | K | L | M | N |
| Alachlor (94%) | 54.66 | 54.66 | 51.24 | 48.79 | 52.99 | 50.38 | 38.67 |
| Polyurea Shell Wall | 5.47 | 5.47 | 5.12 | 4.88 | 5.30 | 5.04 | 3.87 |
| Reax 88B | 1.10 | — | 1.03 | 0.98 | 1.06 | 1.00 | 0.77 |
| Daxad 17 | — | 1.10 | — | — | — | — | — |
| K glyphosate (79% a.e.) | 25.96 | 25.96 | — | — | — | — | — |
| Na glyphosate (86% a.e.) | — | — | 22.45 | 21.38 | 23.22 | 22.07 | 16.94 |
| NaCl | — | — | 2.19 | 2.12 | 2.32 | 2.19 | — |
| (NH₄)₂SO₄ | — | — | — | — | — | — | 30.10 |
| Witconate AOS (100%) | 10.28 | 10.28 | 8.97 | 8.54 | 5.83 | 5.49 | 7.27 |
| Duponol C | — | — | 3.26 | 3.18 | 3.45 | 3.28 | — |
| Petro Ag Special | — | — | 3.54 | 3.36 | 3.63 | 3.64 | — |
| SAG 47 | 0.53 | 0.53 | 0.18 | 0.19 | 0.20 | 0.17 | 0.38 |
| Hisill 233 | — | — | — | 4.58 | — | 4.73 | — |
| H₂O | 2.00 | 2.00 | 2.02 | 2.00 | 2.00 | 2.01 | 2.00 |
| | 100.00 | 100.00 | 100.00 | 100.00 | 100.00 | 100.00 | 100.00 |

The product characteristics of the spray-dried water dispersible granules of Formulations H-N are shown in Table III.

| Reax 88B | 0.48 | |
| (NH₄)₂SO₄ | 25.23 | |
| Arquad 16/29 (28.8) | 3.65 | (1.05 100% active) |
| Hisill 233 | 0.61 | |
| Water | 36.20 | |

TABLE III

| | PRODUCT CHARACTERISTICS FOR FORMULATIONS H-N | | | | | |
|---|---|---|---|---|---|---|
| Formulation | % Retention on 200 mesh | Reconstitution | Wetting | Redispersion | Mesh limits of 95% granules | Shelf Storage |
| H | 0.3 | good | slow | good | 30/80 | good |
| I | 0.2 | excellent | slow | good | 30/80 | good |
| J | 0.4 | good | slow | poor | 30/80 | good |
| K | 0.1 | good | slow | good | 30/80 | good |
| L | 0.5 | good | slow | good | 30/80 | good |
| M | 0.2 | good | slow | good | 30/80 | good |
| N | 0.1 | excellent | slow | excellent | 30/80 | good |

Mesh Size
35 mesh = 500 microns
60 mesh = 250 microns
80 mesh = 180 microns
100 mesh = 150 microns
200 mesh = 74 microns

EXAMPLE 10

This example will describe the preparation of water-dispersible granules comprising encapsulated alachlor -continued

| FEEDSTOCK O | |
|---|---|
| Ingredients | % By Weight |
| Total: | 100.00 |

1. Trimethylhexadecyl ammonium chloride—29% active aqueous.

Formulation O had a total solids content of 61:20%. The alachlor:glyphosate weight ratio is 2.5:1.0.

Feedstock O was then spray dried using a single-fluid hollow-cone nozzle, oriface B-54 and core B-425. Inlet tower temperature was 246°C.; outlet temperature of 118° C.

The composition of the dried granules was as follows:

| FORMULATION O | |
|---|---|
| Ingredient | % by Weight |
| Alachlor (94%) | 35.79 |
| NH$_4$ Glyphosate (90% Glyphosate) | 15.02 |
| Polyurea Shell Wall | 3.58 |
| Reax 88B | 0.77 |
| (NH$_4$)$_2$SO$_4$ | 40.57 |
| Arquad 16/29 | 1.69 |
| Hisill 233 | 0.98 |
| Water | 1.60 |
| Total: | 100.00 |

The water-dispersible granules of feedstock O were dry, free-flowing, non-caking and exhibited excellent reconstitution and dispersion when mixed with water. Bulk density of the granules was 35.24 mg/m$^3$.

EXAMPLE 11

This example describes an embodiment for the encapsulation of alachlor herbicide in a polyurea shell wall followed by admixture with the water-soluble monoammonium salt of glyphosate to form an aqueous feedstock which is then oven-dried to form water-dispersible granules.

In the first stage of the process, an aqueous suspension of alachlor was produced in the manner described in Example 8. That suspension was then fed to a holding tank where said glyphosate salt and formulation adjuvants were added to form the feedstock (Feedstock M), which was filtered through a 100 mesh high-speed vibration filter to remove any foreign material. Feedstock M had the following composition:

| FEEDSTOCK M | |
|---|---|
| INGREDIENT | PERCENT BY WEIGHT |
| Alachlor (94%) | 30.00 |
| Glyphosate (89%; NH$_4$ salt) | 12.63 |
| Polyurea shell wall | 3.0 |
| REAX 88B | 0.60 |
| SAG 780 | 0.30 |
| (NH$_4$)$_2$ SO$_4$ | 27.87 |
| Witconate AOS (90%) | 3.10 |
| Water | 22.50 |
| TOTAL | 100.00 |

The above formulation had a solids content of 72.13%. The alachlor: glyphosate weight ratio is 2.5:1.0.

Feedstock M was air-dried to extrusion consistency (13% H$_2$O), extruded through a 30 mesh screen (U.S. Std.), oven dried overnight at 60° C., then reduced to 20/30 mesh granules.

The composition of the dried granules (Formulation M) was as follows:

| FORMULATION M | |
|---|---|
| INGREDIENT | PERCENT BY WEIGHT |
| Alachlor (94%) | 40.76 |
| Glyphosate (89%, as NH$_2$ salt) | 17.16 |
| Polyurea shell wall | 4.08 |
| REAX 88B | 0.81 |
| SAG 780 | 0.41 |
| (NH$_4$)$_2$ SO$_4$ | 30.56 |
| Witconate AOS (90%) | 4.21 |
| Water | 2.01 |
| TOTAL: | 100.00 |

The water-dispersible granules of Feedstock M exhibited excellent reconstitution and dispersion when mixed with water. Bulk density of the dried granules was 62.472 kg/m$^3$ and the granules were a dense mixture which provides for rapid wetting.

Following substantially the same procedure exemplified above and variations thereof as described herein as to microencapsulation processes, spray-dry modes, etc., one may prepare a wide spectrum of combination pesticides. For example, mixtures of herbicides may be prepared wherein a water-insoluble compound is microencapsulated, while another water-insoluble compound having different properties than the encapsulated compound, e.g., melting points, etc., remains nonencapsulated. Or, a mixture of water-insoluble herbicides may be microencapsulated and further mixed with nonencapsulated water-insoluble herbicides. The spray-dried, water-dispersible granules so prepared and possessing the properties of free-flowing, non-caking, non-dusting, spontaneous reconstitution in water provide all the above-mentioned benefits and advantages.

As mentioned above, the microencapsulation/granulation systems herein provide for the presence of formulation additives to aid in these operations to provide the ultimate water-dispersible granule product. Additional additives are discussed in more detail below.

In general, the emulsifiers found to be useful in the preparation of the formulations of this invention include ligno sulfonates, alkyl naphthalene sodium sulfonates, e.g., Petro AGS, manufactured by Petro Chemicals Co., Inc., lauryl sulfate, sodium lauryl sulfate, manufactured by E. I. DuPont, α-olefin sulfonates such as Witconate AOK (90% flake) and Witconate AOS (39% solution), manufactured by Witco Co., taurates, block copolymers of polyethylene/propylene, quaternary ammonium salts, e.g., Arquad ® and Duoquad ®, manufactured by Armak Chemicals, and other surfactants of solid or near-solid consistency.

There are many commercially available salts of lignin sulfonate which may be conveniently employed and many are described in *McCutcheon's Detergents and Emulsifiers*, North American Edition, 1978, McCutcheon Division, McCutcheon Publishing Company, Glen Rock, N.J. Exemplary of such commercially available lignin sulfonates are Treax ® LTS, LTK, and LTM; respectively, the potassium, magnesium, and sodium salts of lignosulfonate, manufactured by Scott Paper Company, Forest Chemical Products; Marasperse CR ® and Marasperse ® CBOS-3, sodium lignosulfonate, American Can Company, Chemical Products Department, Greenwich, Conn. 06830; Polyfon ® O, H, T, and F and Reax® 85B and 88B, all of which are sodium lignosulfonates manufactured by Westvaco-Polychemicals, Charleston Heights, S.C. 29405.

Other anionic surfactants which have been found to be useful herein are certain taurate surfactants like sodium N-cyclohexyl-N-palmitoyl taurate, sodium N-methyl-N-oleoyl taurate, respectively, sold under the tradename, Igepon CN-42, Igepon T-33, T-43, T-51, T-73, T-77, and T-74 by GAF Corporation, Chemical Products, New York, N.Y., 10020. Sodium N-methyl-N-oleoyl taurate is also available under the tradename "Adinol" from Croda Chemicals, Ltd., England. Preferred for use herein is sodium N-methyl-N-oleoyl taurate.

The anionic surfactant present in the aqueous suspension of microcapsules prior to spray drying to obtain the formulation of the present invention is from about 0.5 percent to about 5.0 percent by weight of the composition, preferably at from about 1.0 to about 3.5 percent by weight and most preferably at about 2.50 percent by weight. In the formulations of this invention, the anionic surfactant may be used in combination with a nonionic block copolymer.

The nonionic block copolymer surfactants particularly useful in preparing formulations of the present invention are polyoxypropylene/polyoxyethylene block copolymers which are condensates of ethylene oxide with the hydrophobic bases formed by condensing propylene oxide with propylene glycol. Such surfactants have the general formula:

$$HO(CH_2CH_2O)_C(\underset{\underset{CH_3}{|}}{C}HCH_2O)_A(CH_2CH_2O)_BH$$

A is a whole number from about 10 to about 70; B and C are whole numbers, the sum of which will range from about 10 to about 350. Exemplary of such surfactants are Pluronic® P103, P104, P105, and Pluronic F108, which are manufactured by BASF Wyandotte Corporation, Industrial Chemicals Group, Wyandotte, Mich., 48192.

The nonionic block copolymer used in the preparation of the formulations of the present invention at from about 0.75 percent to about 5.0 percent by weight of the composition, preferably at from about 1.25 percent to about 4.0 percent and most preferably at about 1.75 percent by weight of the total formulation.

As used herein, the term "hydrated amorphous silicon dioxide" refers to a finely-divided silica such as naturally occurring Kieselguhr or an artificial silica. Artificial silica is silica which has been produced by a chemical reaction as compared with naturally occurring silica such as Kieselguhr. Preferred for use herein are artificial silicas as, for example, artificial silicas sold under the tradename, "Hi-Sil 233" (manufactured by PPG Industries, Inc., Pittsburgh, Pa., 15222) and "Eeo-free 80" (manufactured by J. M. Huber Corporation, Edison, N.J., 08817). There is suitably used at from about 1.0 to about 4.0 percent by weight of the total aqueous composition containing said microcapsules of pesticide dispersed therein, preferably from about 1.5 to about 3.0 percent by weight and most preferably about 2.0 percent by weight, of silica in the form of water-free or hydrated silica gel or other amorphous silica.

The term "hydrated aluminum silica" as used herein refers to such materials as barden clay or kaolin, which are low surface area materials which have an electrostatic surface charge and thus are able to enhance the stability of the dispersion of microcapsules in the liquid phase. These materials are commercially available from many sources as will be readily recognized by those skilled in the art. The "hydrated aluminum silica" component of the formulation described herein is present at from about 0.25 to about 3.0 percent by weight, preferably from about 0.25 to about 1.5 percent by weight and most preferably at 0.5 percent by weight of the total composition.

Suitable formulation adjuvants herein include suitable mono- and polyvalent salts which serve a plurality of functions both in the aqueous suspension feedstock and/or in the dried water-dispersible granules. For example, some of these salts act as flocculents to cause the solids in the aqueous suspension to form small, loosely aggregated bits or particles suspended in the liquid in the composition. Upon spray drying of the liquid composition, these materials serve to function as binders/separators/anti-caking/detack-ifying, etc. agents in the water-dispersible granules formulation of the invention. Suitable salts which may be mentioned are NaCl, CaCl$_2$, MgCl$_2$, Ca(NO$_3$)$_2$, Mg (C$_2$H$_3$O$_2$)$_2$, MgSO$_4$. Other additives include naphthalene salts, Witconate 90, Al(SO$_4$)$_3$.18H$_2$O, (NH$_4$)$_2$SO$_4$, NaNO$_3$, and the like. Preferred for use herein is CaCl$_2$, NaCl, Witconate 90 and (NH$_4$)SO$_4$ or combination of the latter two, preferably in ratios above 1:1, typically 1:2 to 1:3, especially 1:2.5 (Witconate:(NH$_4$)$_2$SO$_4$). A combination of sodium and calcium chlorides in a 1:2 ratio is another preferred embodiment. The adjuvant content in the water-dispersible granule is from about 0.5 percent to about 25.0 percent by weight, preferably at from about 1.0 to about 15.0 percent by weight and most preferably at 1.00-10.0 percent by weight of total composition. As would be recognized by one skilled in the art, the salt will also act to depress the freezing point of the aqueous liquid and thus will act as an anti-freeze agent, should one wish to store the liquid suspension of microcapsules prior to spray drying.

Lower alkyl glycols, e.g., ethylene or proplyene glycol, are examples of suitable anti-freeze agents useful in the suspension of microcapsules described herein and act as anti-caking agents in the water-dispersible granule. Amounts of these components ranging from about 2.0 percent to about 10.0 percent by weight of the total composition will adequately provide the composition with the desired antifreeze protection and anti-caking action. Suitably, from about 2.0 to about 5.0 percent by weight of the glycol will be present in the formulation, preferably, about 2.5 percent by weight of the anti-caking agent is used in the formulation of the present invention.

Minor quantities, i.e., from 0 to about 5.0 percent by weight of total composition, of one or more other inert formulation adjuvants such as anti-foaming agents, anti-caking agents, biocides, dyes, anti-corrosion agents, acids or bases to adjust pH, and the like, may be incorporated into the liquid suspension of microcapsules prior to spray drying to obtain the water-dispersible granular formulation of the present invention, especially if the liquid suspensions for said formulations are to be stored for any extended period of time prior to spray drying, particularly under adverse storage conditions.

As indicated above, the water-dispersible granules herein may contain up to 75% or more by weight of the active ingredient, the balance being made up of binders/separators/dispersants/anti-caking, etc. formulation additives.

It will be understood by those skilled in the art that some experimentation may be in order to ascertain which of certain suspension adjuvants or agglomeration adjuvants perform most suitably considering the nature of active ingredients and other formulation additives. Similarly, some experimentation within the skill of the art may be necessary to ascertain the level of encapsulability of higher-melting water-insoluble components and/or the drying capacities of relevant aqueous suspensions containing the granules feedstocks.

Finally, as will be appreciated by those skilled in the art, the practice of this invention may readily be adapted to the production and formulation of water-dispersible granules of a wide variety of materials having countless uses. For example, it is within the purview of this invention to produce water-dispersible granules of pharmaceutical compounds, detergents, dyes, inks, etc., etc.

What is claimed is:

1. Water-dispersible dry granules comprising:
   (a) a water-disintegrable aggregation of a plurality of essentially-spherical microcapsules encapsulating at least one water-insoluble herbicide, fungicide, insecticide, or plant growth regulant within a polymeric shell wall,
   (b) particles of at least one water-soluble or water-regulant non-encapsulated herbicide, fungicide, insecticide, or plant growth regulant, holding the microcapsules together to form the granules,
   (c) no more than about 8% by weight moisture, and, optionally,
   (d) formulation adjuvants.

2. Granules according to claim 1 wherein said microcapsules and particles of components (a) and (b) are essentially spherical and from about 150 to 850 microns in diameter.

3. Granules according to claim 2 wherein said microcapsules and particles are within the range of from about 250–450 microns in diameter.

4. Granules according to claim 3 wherein the bulk density is within the range of from about 32 to about 96 kg/m$^3$.

5. Granules according to claim 4 wherein said bulk density is within the range of about 56 to about 72 kg/m$^3$.

6. Granules according to claim 1 wherein said components (a) and (b) are both herbicides.

7. Granules according to claim 6 wherein component (a) is a water-insoluble herbicide.

8. Granules according to claim 7 wherein component (a) is an acetanilide herbicide.

9. Granules according to claim 8 wherein said acetanilide is selected from the group consisting of alachlor, butachlor, acetochlor, metolachlor, metazochlor, $\alpha$-chloro-N-(ethoxymethyl)-N-[2-methyl-6-(trifluoromethyl)-phenyl] acetamide and $\alpha$-chloro-N-(2-methoxy-6-methylphenyl)-N-(1-methylethoxymethyl)acetamide.

10. Granules according to claim 9 wherein component (b) is a water-insoluble herbicide.

11. Granules according to claim 10 wherein the herbicide of component (b) is selected from the group consisting of atrazine and imazaquin.

12. Granules according to claim 11 wherein the herbicide of component (a) is alachlor and the herbicide of component (b) is atrazine.

13. Granules according to claim 1 wherein said herbicide, fungicide, insecticide or plant growth regulant constitute an effective amount up to 90% by weight.

14. Granules according to claim 13 wherein the ratio of component (a) to component (b) is within the range of about 50:1 to 1:50.

15. Granules according to claim 14 wherein said ratio is within the range of about 20:1 1:1.

16. Granules according to claim 15 wherein said ratio is within the range of 16:1 to 1:1.

17. Granules according to claim 1 wherein said component (d) includes as binders/separators for said components (a) and (b) an alkali metal salt, an alkaline earth metal salt, ammonium sulfate or a Witconate salt or other adjuvant or combinations thereof.

18. Granules according to claim 17 wherein said binder/separator is a combination of ammonium sulfate and a Witconate salt in ratios within the range of about 1:1 to 24.0:1.0.

19. Granules according to claim 18 wherein said ratio is about 2.5:1.0.

20. Granules according to claim 17 wherein said binder/separator is combination of sodium and calcium chlorides.

21. Granules according to claim 19 wherein the moisture content is no greater than about 4.0% by weight of said formulation.

22. Granules according to claim 21 wherein said moisture content is between about 1.0–2.0% by weight of said formulation.

* * * * *